United States Patent
Ohta et al.

(10) Patent No.: US 8,314,397 B2
(45) Date of Patent: Nov. 20, 2012

(54) RADIOGRAPHIC IMAGING DEVICE

(75) Inventors: Yasunori Ohta, Kanagawa (JP);
Naoyuki Nishino, Kanagawa (JP);
Naoto Iwakiri, Kanagawa (JP);
Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/948,778

(22) Filed: Nov. 18, 2010

(65) Prior Publication Data

US 2011/0121190 A1   May 26, 2011

(30) Foreign Application Priority Data

Nov. 20, 2009  (JP) .................................. 2009-265197
Oct. 26, 2010  (JP) .................................. 2010-239995

(51) Int. Cl.
*G01T 1/24* (2006.01)
(52) U.S. Cl. ................................................ 250/370.08
(58) Field of Classification Search .............. 250/370.08
See application file for complete search history.

(56) References Cited

U.S. PATENT DOCUMENTS 6,434,218 B1 *  8/2002  Matsumoto ................... 378/155
2006/0054822 A1 *  3/2006  Tsuchino .................. 250/336.1

FOREIGN PATENT DOCUMENTS

| JP | 2000-10220 A | | 1/2000 |
|---|---|---|---|
| JP | 2000010220 A | * | 1/2000 |
| JP | 2003-339687 A | | 12/2003 |
| JP | 2004-173908 A | | 6/2004 |
| JP | 2009-032854 A | | 2/2009 |
| JP | 2009-80103 A | | 4/2009 |
| JP | 2009-212389 A | | 9/2009 |

* cited by examiner

*Primary Examiner* — Christine Sung
(74) *Attorney, Agent, or Firm* — SOLARIS Intellectual Property Group, PLLC

(57) ABSTRACT

A radiographic imaging device includes: a panel unit accommodating a radiation detection panel; a control unit accommodating a control section and a power source section; and a connection portion, a first end portion of the connection portion being attached to a side portion of the panel unit so as to be rotatable around a first axis that is substantially parallel to an irradiation surface of the panel unit, and a second end portion of the connection portion being attached to the control unit so as to be rotatable around a second axis that is substantially parallel to the first axis.

13 Claims, 14 Drawing Sheets

RADIOGRAPHIC IMAGING DEVICE

CROSS-REFERENCE TO RELATED APPLICATION

This application claims priority under 35 USC 119 from Japanese Patent Applications No. 2009-265197 filed Nov. 20, 2009 and No. 2010-239995 filed Oct. 26, 2010, the disclosure of which is incorporated by reference herein.

BACKGROUND OF THE INVENTION

1. Technical Field

The present invention relates to a radiographic imaging device and, in particular, to a radiographic imaging device equipped with a radiation detection panel.

2. Related Art

Flat panel detectors (FPDs) have become commercially viable in recent years. An FPD includes a radiation-sensitive layer that is placed on a thin film transistor (TFT) active matrix substrate, and the FPD detects incident radiation such as x-rays, directly converts the detected radiation into radiographic image data representing the distribution of the incident radiation amount, and then outputs the data. Portable radiographic imaging devices (also referred to below as electronic cassettes) have also become commercially viable. These devices incorporate a control unit that includes an image memory and a panel-type radiation detector such as an FPD, and a power source unit, and store radiographic image data output from the radiation detector in the image memory. Since an electronic cassette has excellent portability, a subject can be imaged while remaining on a stretcher or a bed and, in addition, since it is easy to adjust the imaging region by changing the position of the electronic cassette, it is possible to flexibly deal with situations where an immobile subject is to be imaged.

Related to the foregoing, Japanese Patent Application Laid-open (JP-A) No. 2003-339687 discloses a technique in which, in an imaging device such as an electronic cassette having a planar sensor, two planar sensors are joined along one of each of their edges in an openable and closable configuration, in order to increase the surface area of the planar sensor while also maintaining both portability and storability, and to realize imaging from plural directions.

JP-A No. 2004-173908 discloses a technique in which, in order to reduce the physical load on the operator, the electronic cassette (imaging unit) is separated from the imaging control unit and is set into a stage of an auxiliary device that is in a vertical state and, at the time of imaging, the stage (the detection surface of the electronic cassette) is raised to an horizontal state by operating an hydraulic cylinder that is connected to the stage.

JP-A No. 2009-80103 discloses a technique in which, in order to reduce the weight of a cassette system, a control unit equipped with electronic parts such as an interface circuit portion, a cassette control portion and a communications unit, is configured such that it can be disposed separately from the cassette holding the radiation detector via a connector and a cable, and the control unit is separated from the cassette at the time of imaging.

JP-A No. 2000-10220 discloses an x-ray imaging device having a configuration in which a panel case provided with an x-ray image detection means and a control case provided with a control means are connected to each other so as to be freely rotatable, with the aims of reducing size and thickness of and protecting the x-ray image detection means during transport and storage.

A radiographic imaging device such as an electronic cassette is configured such that the control unit and the power source unit in particular include a large number of electronic parts, and certain portions use electronic parts that give off a large amount of heat. As a result, there are cases when phenomena such as changes in the electrical properties of the radiation detector (for example, an increase in noise or an increase in TFT dark current) or deterioration of the radiation detector. A patient may become uncomfortable by an excessive increase in the surface temperature of a radiographic imaging device. In particular, when capturing a moving image by radiography, fluoroscopy or the like, since a greater amount of heat is produced as compared with a still image due to the continuous (long-term) image capture that is conducted, the above-mentioned phenomena are exacerbated and it may be necessary to devise measures, such as limiting the time of continuous operation, that may ultimately reduce the ease of use of the device.

In addition, examples of deterioration of a radiation detector include deformation or breakage caused by differences in the thermal expansion coefficient of respective members in a radiation detector having a layered structure and deterioration or separation of an adhesive caused by repeated temperature change. Further, when a radiation detector has a configuration that includes amorphous selenium, crystallization of the amorphous selenium may occur in conjunction with temperature increase in the radiation detector. Further, when a radiation detector has a configuration that includes a scintillator layer formed from CsI, the sensitivity of radiation detection may decrease in conjunction with temperature increase. The sensitivity of CsI changes at a sensitivity change rate of approximately 0.3% per 1° C. of temperature change, for example. As a result, since there is a high degree of temperature change when, for example, capturing a moving image by radiography, fluoroscopy or the like, which causes a large change in sensitivity, there is a large difference between the density of images captured toward the beginning of the period of image capture and images captured toward the end of the image capture period, which creates the possibility of problems such as deterioration in the visibility of moving images and reduced accuracy of diagnoses from moving images.

In this regard, the above-mentioned JP-A No. 2009-80103 proposes providing a means for cooling the radiation detector inside the cassette in order to suppress structural changes (crystallization) in the amorphous selenium that forms a part of the radiation detector. However, this is problematic in that the configuration of the radiographic imaging device becomes complicated and the installation of the cooling means may lead to an increase in the amount of power consumed by the radiographic imaging device. Further, the techniques described in JP-A Nos. 2003-339687, 2004-173908 and 2000-10220 give no consideration to heat dissipation or cooling.

SUMMARY

In view of the foregoing circumstances, the present invention provides a radiographic imaging device that enables temperature increase of a radiation detection panel to be suppressed without causing any complication of configuration or increase in electrical power consumption.

A radiographic imaging device of a first aspect of the present invention includes: a panel unit accommodating a radiation detection panel; a control unit accommodating a control section and a power source section; and a connection portion, a first end portion of the connection portion being attached to a side portion of the panel unit so as to be rotatable around a first axis that is substantially parallel to an irradiation surface of the panel unit, and a second end portion of the connection portion being attached to the control unit so as to be rotatable around a second axis that is substantially parallel to the first axis.

The radiographic imaging device of the first aspect is divided into a panel unit accommodating a radiation detection panel and a control unit accommodating a control section and a power source section, and the respective units are connected via a connection portion. Further, a first end portion of the connection portion is attached to a side portion of the panel unit so as to be rotatable around a first axis that is substantially parallel to an irradiation surface of the panel unit, and a second end portion of the connection portion is attached to the control unit so as to be rotatable around a second axis that is substantially parallel to the first axis. As a result, when both ends of the connection portion rotate relative to the respective units, the panel unit and the control unit move relative to each other and the distance between the respective units changes. By performing image capture in a state in which the panel unit and the control unit are separated at a certain distance from each other that is, a state in which thermal coupling between the respective units is low, it is less likely that the radiation detection panel accommodated in the panel unit will be affected by heat generated at the control section and the power source section accommodated in the control unit, whereby increases in the temperature of the radiation detection panel are suppressed.

Further, at times when image capture is not performed, such as during storage or transport, a state in which the distance between the panel unit and the control unit is minimized or nearly minimized, such as a state in which the respective units are stacked one on the other, is preferable. The outer peripheral dimensions of the radiographic imaging device are thereby minimized or nearly minimized and ease of handling is increased. By changing the distance between the panel unit and the control unit by rotation of both ends of the connection portion relative to the respective units, it is possible to switch between a state in which the radiation detection panel is less likely to be affected by heat generated at the control section and the power source section and a state in which the outer peripheral dimensions of the radiographic imaging device are minimized or nearly minimized. As a result, increases in temperature of the radiation detection panel during image capture can be suppressed without providing a cooling means inside the panel unit. Accordingly, the configuration of the radiographic imaging device is not made more complicated and electrical power consumption is not increased.

In a second aspect of the present invention, a configuration may be adopted in which, in the radiographic imaging device of the first aspect, the radiation detection panel detects radiation that has transmitted through an imaging subject and irradiated the irradiation surface of the panel unit and the control section includes a drive section that drives the radiation detection panel such that a radiographic signal is output by the radiation detection panel, and a signal processing section that converts the radiographic signal output by the radiation detection panel to radiographic image data expressing the distribution of an irradiated radiation dose and outputs the radiographic image data.

In a third aspect of the present invention, a configuration may be adopted in which, in the radiographic imaging device of either of the above aspects, the connection portion is rotatable between a first state in which the irradiation surface of the panel unit contacts the control unit and a second state in which a side portion of the panel unit and a side portion of the control unit face each other with a gap therebetween. As a result, in the first state, at least a part of the irradiation surface of the panel unit is covered by the control unit and the irradiation surface can be protected from damage such as scratches. Further, in the first state, a state in which the entire surface of the irradiation surface of the panel unit is covered by the control unit is preferable. This enables the entire surface of the irradiation surface to be protected from damage such as scratches in the first state.

In a fourth aspect of the present invention, a configuration may be adopted in which, in the radiographic imaging device of the third aspect, at least one of the first end portion or the second end portion of the connection portion is movably attached to the panel unit or the control unit and, in the second state, at least one of the panel unit or the control unit moves relatively in accordance with movement of the connection portion.

This is achieved, for example, by attaching at least one of the first end portion or the second end portion of the connection portion to a long hole provided at the panel unit or the control unit. The long hole may be configured such that the direction of relative movement between the panel unit and the control unit is a length direction. As a result, the distance between the panel unit and the control unit in the second state can be increased beyond a length governed by the length of the connection portion and thermal coupling between the respective units during image capture may be even further reduced.

In a fifth aspect of the present invention, a configuration may be adopted in which, in the radiographic imaging device of the fourth aspect, a range of movement of the at least one of the first end portion or the second end portion of the connection portion relative to the panel unit or the control unit is set such that, in the second state, the panel unit or the control unit is rotatable around the first axis or the second axis without being impeded by the other of the panel unit or the control unit. As a result, the positional relationship between the front and rear of the panel unit and of the control unit can be changed as desired by rotation of either the panel unit or the control unit in the second state.

In a sixth aspect of the present invention, a configuration may be adopted in which, in the radiographic imaging device of the first through fifth aspects, the control section accommodated in the control unit further includes a communications section that communicates with the exterior. As a result, it is possible to send radiographic image data obtained from radiation detection by the radiation detection panel to the exterior and to receive radiographic image data captured in the past or other information from an external source. Further, communications by the communications section may be wired or wireless.

In a seventh aspect of the present invention, a configuration may be adopted in which, in the radiographic imaging device of the first through sixth aspects, the control unit is provided with a display portion that is configured to display information; and the control section accommodated in the control unit further includes a display control section that is configured to effect display of information at the display portion. As a result, it is possible to display a radiographic image expressing data obtained from radiation detection at the display portion. Further, when a communications section is provided, it is possible to display radiographic image data captured in the past or other information that has been received from an external source at the display portion.

In an eighth aspect of the present invention, a configuration may be adopted in which, in the radiographic imaging device of the third through fifth aspects, a display portion that is configured to display information is provided such that a display screen is exposed at an external peripheral portion of the control unit; the control section accommodated in the control unit further includes a display control section that is configured to effect display of information at the display portion; and, in the first state, the display portion of the control unit contacts the irradiation surface of the panel unit. Similarly to in the seventh aspect of the invention, it is possible to display a radiographic image expressing data obtained from radiation detection by the radiation detection panel at the display portion. Further, since a planar portion of the control unit contacts the irradiation surface of the panel unit in the first state, the display portion is protected from breakage or other damage in addition to the irradiation surface of the panel unit being protected from scratching or other damage.

In a ninth aspect of the present invention, a configuration may be adopted in which, in the radiographic imaging device of the seventh or eighth aspect, the control section in the control unit further includes a storage section that is adapted to store information including radiographic image data; and the display control section effects display of the information including radiographic image data stored at the storage section, at the display portion. As a result, it is possible for various information such as information explaining imaging procedure as well as radiographic image data to be stored in the storage section are displayed at the display portion.

In a tenth aspect of the present invention, a configuration may be adopted in which, in the radiographic imaging device of the ninth aspect, the control unit is provided with an input portion for inputting information; and the display control section selects information to be displayed at the display portion based on information input via the input portion. As a result, it is possible for any necessary information to be displayed at the display portion by operation of the input portion by the operator of the radiographic imaging device. Further, the input portion may be a numeric keypad, a keyboard, a switch or the like provided at the control unit separately from the display portion or a touch panel or the like provided at the display portion.

In an eleventh aspect of the present invention, a configuration may be adopted in which, in the radiographic imaging device of the first through tenth aspects, the radiation detection panel includes a radiation conversion layer and a switching layer, in which a substrate that forms the switching layer is formed from a material through which radiation transmits. When the radiation detection panel includes a radiation conversion layer and a switching layer, it is normal to dispose the radiation detection panel for image capture such that radiation is incident from the side of the radiation conversion layer; however, if the substrate that forms the switching layer is formed from a material through which radiation transmits, the radiation detection panel may be disposed for image capture such that radiation is incident from the side of the switching layer.

In a twelfth aspect of the present invention, a configuration may be adopted in which, in the radiographic imaging device of the first through eleventh aspects, the radiation detection panel includes a light emitting portion that absorbs radiation and emits light and a detection portion that detects light emitted from the light emitting portion, and the light emitting portion has a columnar crystal structure portion. As a result, light that is emitted as a result of absorption of radiation by the light emitting portion is channeled along gaps in the columnar crystal structure portion and emitted toward the side of the detection portion, whereby diffusion of light emitted toward the detection portion side is suppressed and blurring of radiographic images detected by the radiation detection panel can be suppressed.

In a thirteenth aspect of the present invention, a configuration may be adopted in which, in the radiographic imaging device of the twelfth aspect, the light emitting portion that has a columnar crystal structure portion includes CsI.

In a fourteenth aspect of the present invention, a configuration may be adopted in which, in the radiographic imaging device of the first aspect, the panel unit and the control unit are rotatably connected with the two connection portions attached therebetween.

BRIEF DESCRIPTION OF THE DRAWINGS

Embodiments of the present invention will be described in detail based on the following figures, wherein.

DETAILED DESCRIPTION OF THE INVENTION

In the following, an example of an exemplary embodiment of the present invention will be described in detail with reference to the drawings.

First Exemplary Embodiment

Figure 1A:
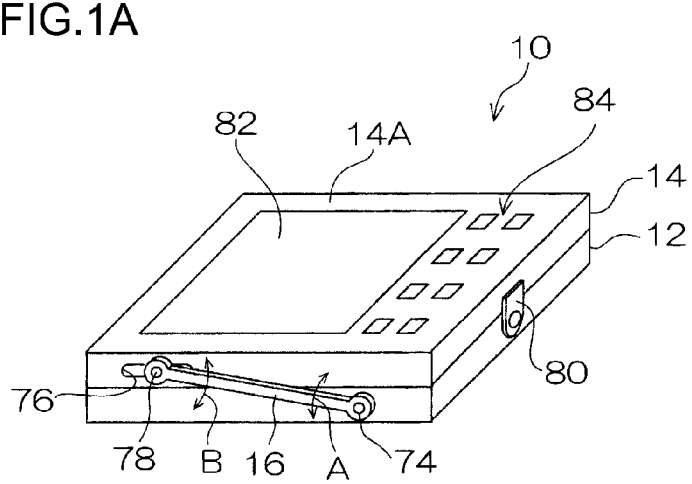
FIGS. 1A-1C are perspective views showing the outer appearance of an electronic cassette according to a first exemplary embodiment.
Figure 1B:
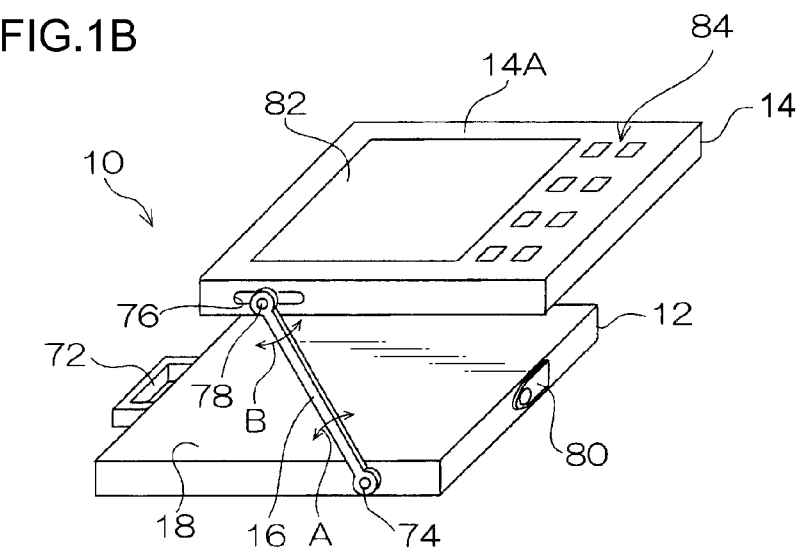
Figure 1C:
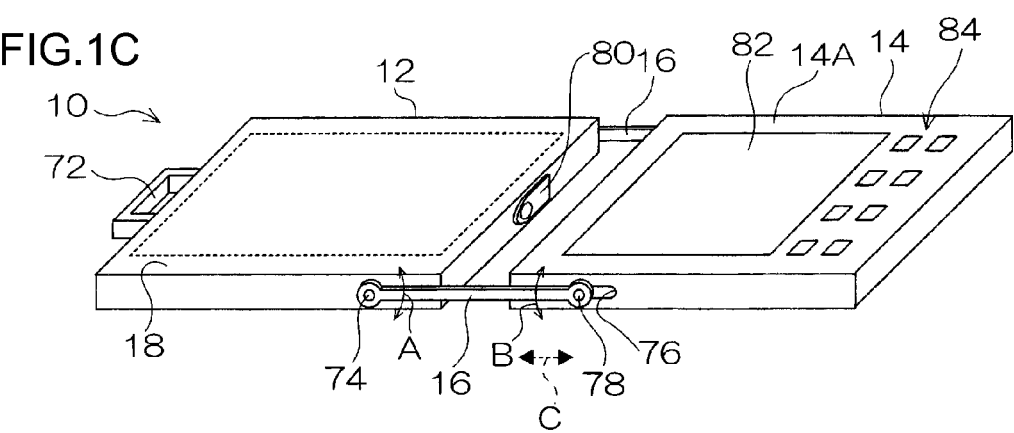

FIGS. 1A to 1C show electronic cassette 10 according to the first exemplary embodiment. The casing of electronic cassette 10 is divided into panel unit 12 that houses planar radiation detection panel 20 (refer to FIG. 2) and control unit 14 that houses control section 50 and power source section 70 (refer to FIG. 2), which are also planar, and other parts, and panel unit 12 and control unit 14 are connected via a pair of connection rods 16.

In a state in which panel unit 12 and control unit 14 are stacked one on the other as shown in FIG. 1A (a storage state), the surface of panel unit 12 that contacts control unit 14 is irradiation surface 18 which is irradiated by radiation at the time of imaging. Handle portion 72 for holding when electronic cassette 10 is carried is attached to one of four side surfaces of panel unit 12 adjacent to irradiation surface 18. Further, among the four side surfaces of panel unit 12, at the opposing pair of side surfaces to which handle portion 72 is not attached, pin 74 is provided substantially orthogonal to the pair of side surfaces. One end portion of each of the pair of connection rods 16 is attached to the pair of side surfaces of panel unit 12 via pin 74 so as to be rotatable around pin 74 (in the direction of arrow A in FIG. 1); the direction of arrow A is an example of "around a first axis" in the present invention.

Further, long holes 76 are provided along a length direction in each of opposing side surfaces of control unit 14 that are adjacent to the side surfaces of panel unit 12 to which one end portion of each of the pair of connection rods 16 are attached. The storage state shown in FIG. 1A is an example of a first state as recited in claim 3. The other end portions of the pair of connection rods 16 are respectively attached to pin 78, which projects in a direction substantially orthogonal to the pair of side surfaces of control unit 14. Pin 78, which is attached to each of the pair of connection rods 16, passes through long holes 76 provided at the side surfaces of control unit 14, and stoppers (not shown in the drawings) having a larger size than the width of long holes 76 are attached to the end portions of pin 78 to prevent pin 78 from coming out of long holes 76. Accordingly, the other end portions of the pair of connection rods 16 are fitted, via pin 78, into long holes 76 at the side surfaces of control unit 14 such that there is play therebetween. The pair of connection rods 16 are rotatable relative to control unit 14 around the axis of pin 78, (in the direction of arrow B in FIG. 1); the direction of arrow B is an example of "around a second axis" in the present invention. The end portions to which pin 78 is attached are movable in a length direction of long holes 76 (direction of arrow C in FIG. 1).

Due to the pair of connection rods 16 rotating relative to panel unit 12 and control unit 14, electronic cassette 10 is able to transition to a stored state (refer to FIG. 1A) in which panel unit 12 and control unit 14 are stacked, or to a deployed state (refer to FIG. 1C; an example of a second state as recited in claim 3) in which panel unit 12 and control unit 14 are placed in the same plane and a side surface of panel unit 12 at which pin 74 is not provided (the side surface at which stopper 80, which is described below, is provided) faces a side surface of control unit 14 at which a long hole 76 is not provided, with a gap therebetween, via an intermediate state (refer to FIG. 1B) in which the surface of control unit 14 that is in contact with irradiation surface 18 in the stored state is separated from and faces irradiation surface 18.

Further, in the deployed state, movement of the end portions of the pair of connection rods 16 in the length direction (the direction of arrow C in FIG. 1) of long holes 76 enables the size of the gap between panel unit 12 and control unit 14 to be adjusted.

Further, stopper 80, which is rotatable between a holding position in which its leading edge projects beyond irradiation surface 18 (the position shown in FIG. 1A) and a release position in which its leading edge is retracted to a position lower than irradiation surface 18 (the position shown in FIGS. 1B and 1C), is provided at the side surface of panel unit 12 to which handle portion 72 is attached as well as the opposing side surface. In FIG. 1, the stopper 80 provided at the side surface of panel unit 12 to which handle portion 72 is attached is omitted from the drawings. When stopper 80 is rotated to the holding position in the above-described storage state, movement of control unit 14 in a direction away from panel unit 12 is prevented and electronic cassette 10 is kept in the storage state.

Figure 2:
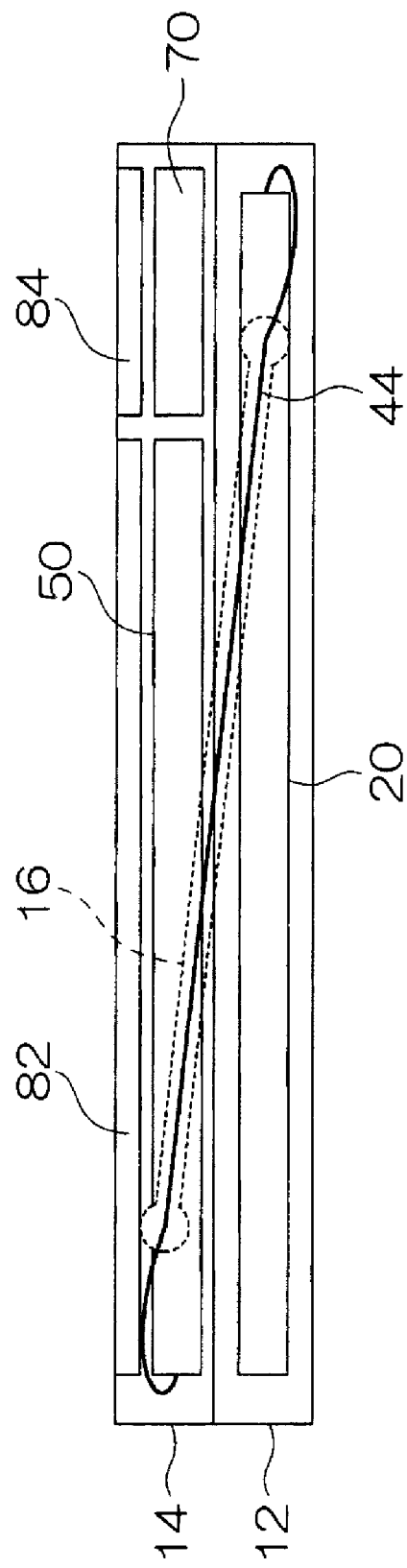
FIG. 2 is a sectional view showing the internal configuration of the electronic cassette according to the first exemplary embodiment.

As shown in FIG. 2, connection wire 44 passes through the inside of connection rod 16. One end of connection wire 44 extends inside panel unit 12 and is connected to radiation detection panel 20, and the other end of connection wire 44 extends inside control unit 14 and is connected to control section 50. Connection wire 44 is of a length that enables a connected state between radiation detection panel 20 and control section 50 to be maintained even when, for example, the size of the gap between panel unit 12 and control unit 14 in the deployed state is adjusted.

Figure 3:
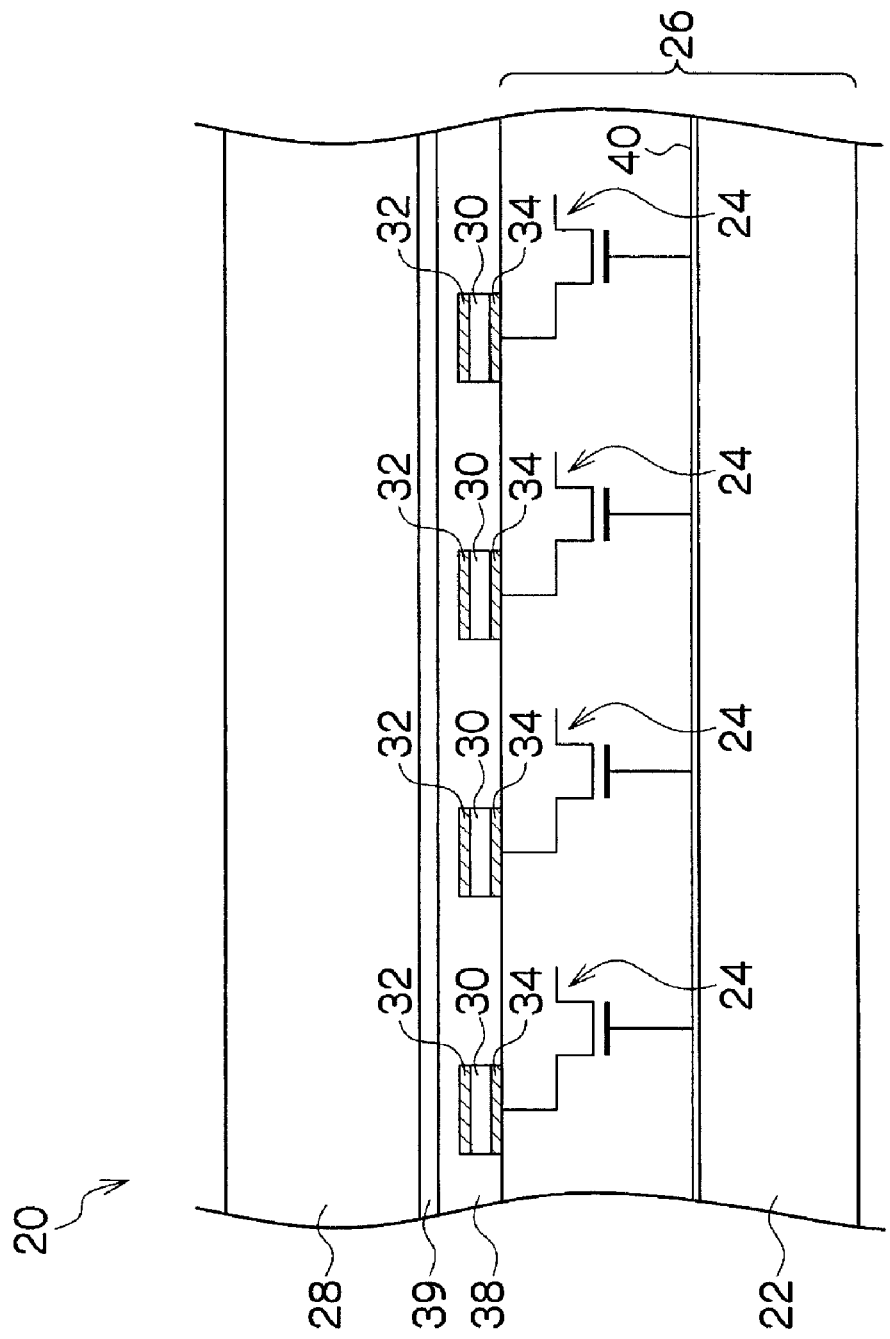
FIG. 3 is a sectional view showing a schematic configuration of a radiation detection panel.

Next, radiation detection panel 20, which is housed inside panel unit 12, is explained. Radiation detection panel 20 detects radiation irradiated onto the surface of panel unit 12, and outputs an electrical signal (radiation detection signal) expressing the distribution in the amount of irradiated radiation. As shown in FIG. 3, TFT substrate 26 is provided, which is formed with switching elements 24 such as thin film transistors (TFTs) to be provided on insulating substrate 22. Glass substrates, various kinds of ceramic substrates, or resin substrates may be used as insulating substrate 22; however, the materials are not limited to these. Scintillator layer 28, which is an example of a radiation conversion layer that converts incident radiation to light, is formed above TFT substrate 26.

In addition, the wavelength of the light emitted from scintillator layer 28 is preferably in the visible light region (a wavelength of 360 nm to 830 nm) and, when a black and white image is captured by radiation detection panel 20, the wavelength region of G (green) is preferably included. Specifically, the fluorescent body used in scintillator layer 28 preferably includes cesium iodide (CsI) when x-rays are used as the radiation and CsI (Tl) (cesium iodide to which thallium has been added) having a luminescence spectrum of 420 nm to 600 nm when irradiated with x-rays is particularly preferable. The luminescent peak wavelength of CsI (Tl) in the visible light region is 565 nm. In addition, other than CsI (Tl), $GOS(Gd_2O_2S)$ may be used as scintillator layer 28; however, the materials are not limited to these.

Figure 4:
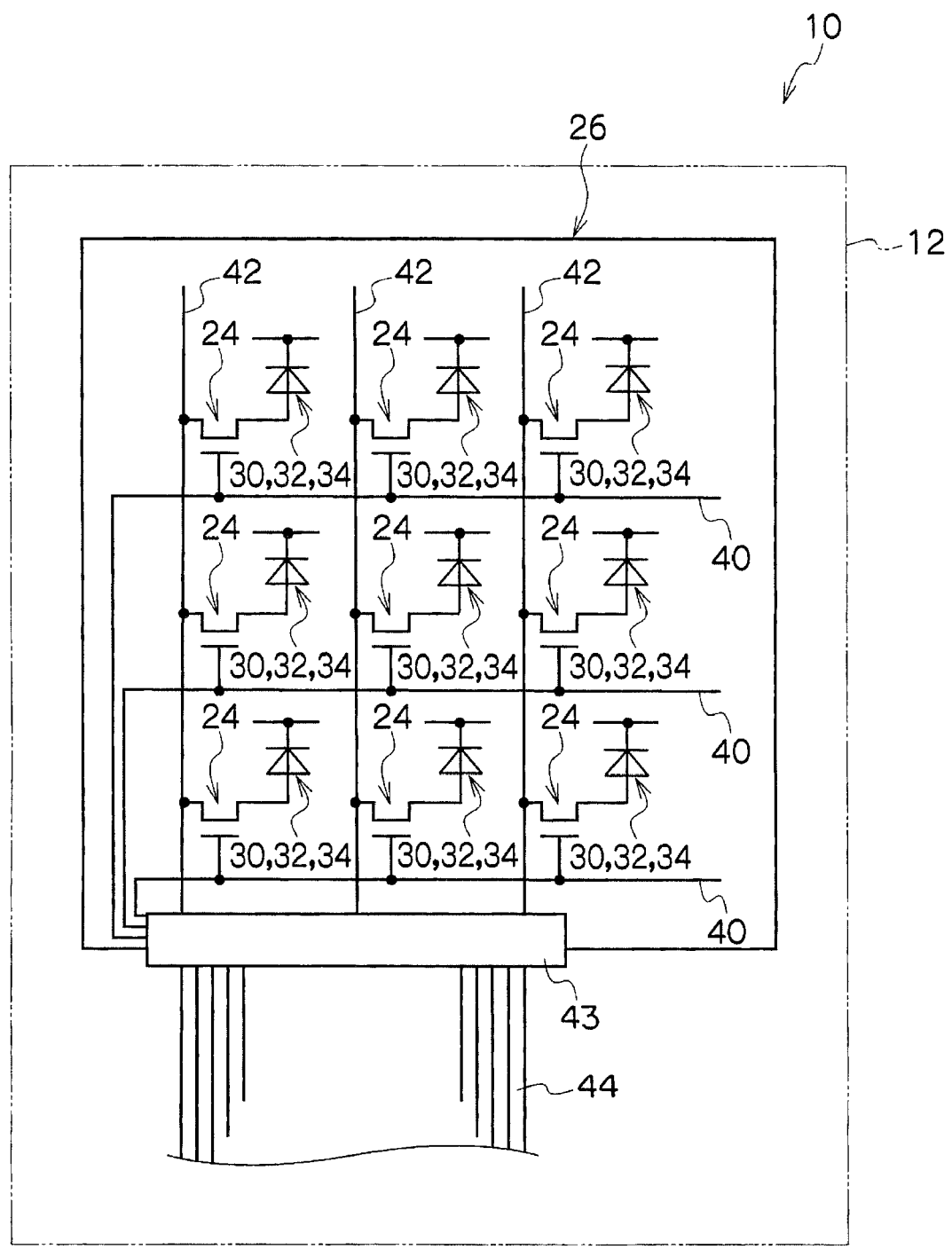
FIG. 4 is a circuit diagram showing a schematic configuration of a radiation detection panel.

Photoconductive layers 30, which generate electrical charge as a result of incident light converted by scintillator layer 28, are disposed between scintillator layer 28 and TFT substrate 26. Bias electrodes 32, which are for applying a bias voltage to photoconductive layers 30, are formed at the surface of photoconductive layers 30 at the side of scintillator layer 28. Charge collection electrodes 34, which collect the charge generated at photoconductive layers 30, are formed at TFT substrate 26. Charge collected at each of charge collection electrodes 34 is read out at TFT substrate 26 by switching elements 24 being turned on. As shown in FIG. 4, charge collection electrodes 34 are disposed at TFT substrate 26 in a two-dimensional arrangement, and switching elements 24 are disposed at insulating substrate 22 in a two-dimensional arrangement in correspondence therewith. Further, radiation detection panel 20 having the layered configuration shown in FIG. 3 is disposed in the panel unit 12 such that the side of scintillator layer 28 is closer to irradiation surface 18 than the side of TFT substrate 26.

Further, as shown in FIG. 4, plural gate wires 40 for turning each of switching elements 24 on and off are provided at TFT substrate 26 so as to extend in a certain direction (a row direction) and plural data wires 42 for reading out charge via switching elements 24 in an on state are provided so as to extend in a direction (a column direction) perpendicular to gate wires 40.

In addition, as shown in FIG. 3, planarization layer 38 is formed on TFT substrate 26 in order to planarize the configuration above TFT substrate 26. Further, adhesive layer 39 is formed on planarization layer 38 between TFT substrate 26 and scintillator layer 28 in order to adhere scintillator layer 28 to TFT substrate 26.

TFT substrate 26 has a quadrilateral shape having four sides at its outer periphery as seen in plan view (more specifically, a rectangular shape) and connection terminal 43 is disposed at one side among the peripheral edge portions of TFT substrate 26 as seen in plan view, to which each of gate wires 40 and each of data wires 42 is connected. Connection terminal 43 is connected to control section 50 via connection wire 44, which is explained above.

Control unit 14 is provided with control section 50 that performs, for example, driving of radiation detection panel 20 and conversion to radiographic image data from radiographic detection signals output from radiation detection panel 20, power source section 70 that supplies electrical power to control section 50, display portion 82 and operation portion 84 formed from plural keys. Display portion 82 is provided with a display surface exposed at display/operation surface 14A on the opposite side from irradiation surface 18 of panel unit 12 in the storage state. Operation portion 84 is provided at display/operation surface 14A.

Figure 5:
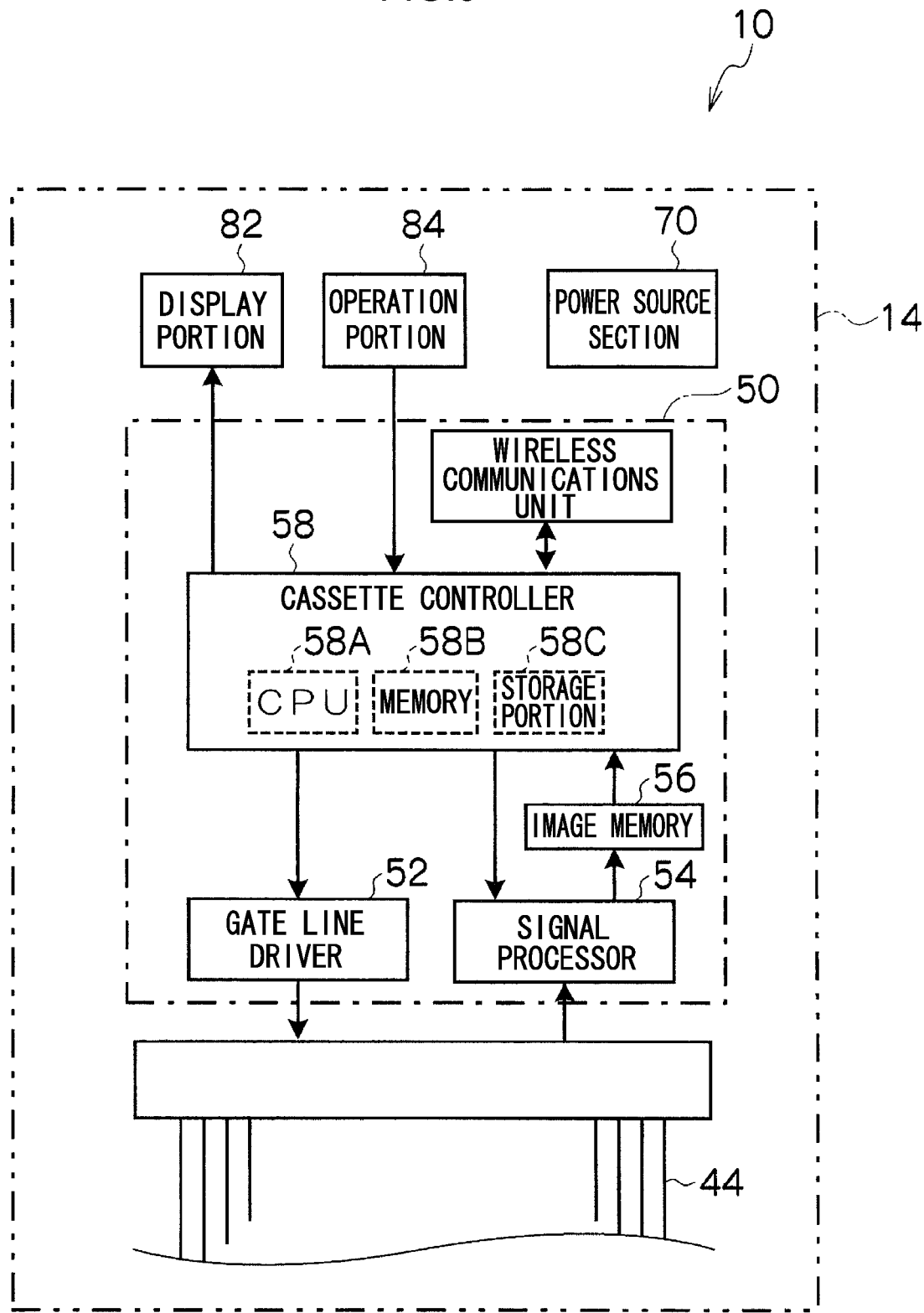
FIG. 5 is a block diagram showing a schematic configuration of the electrical system of the electronic cassette.

As shown in FIG. 5, control section 50 is provided with gate line driver 52, signal processor 54, image memory 56, cassette controller 58, and wireless communications unit 60. Each of switching elements 24 (refer to FIGS. 3 and 4) is switched on in order, row by row, by a signal supplied from gate line driver 52 via gate wires 40, and the charge read out from each switching element 24 in an on state is transmitted via data wires 42 as an electrical signal and input to signal processor 54. As a result, charge is read out in order row by row and a radiographic detection signal representing a two-dimensional radiographic image is obtained. Gate line driver 52 is an example of a drive section as recited in claim 2.

While not shown in the drawings, signal processor 54 is equipped with an amplifier circuit that amplifies the input electrical signal and a sample-and-hold circuit provided for each of the data wires 42, and the electrical signal transmitted via each of data wires 42 is amplified by the amplifier circuit and held at the sample-and-hold circuit. A multiplexer and an analogue/digital (A/D) converter are connected to the output side of the sample-and-hold circuits in order, and the electrical signal held at each sample-and-hold circuit is input to the multiplexer in order (serially) and converted to digital image data (radiographic image data) by the A/D converter. Signal processor 54 is an example of a signal processing section as recited in claim 2.

Signal processor 54 is connected to image memory 56 and image data output from the A/D converter of signal processor 54 is stored in order in image memory 56. Image memory 56 has a storage capacity capable of storing radiographic image data for plural images and, whenever radiographic image capture is performed, the captured radiographic image data is stored sequentially in image memory 56. Image memory 56 is an example of a storage section as recited in claim 9.

Image memory 56 is connected to cassette controller 58. Cassette controller 58 is formed from a microcomputer, is equipped with CPU 58A, memory 58B including both ROM and RAM, and non-volatile storage portion 58C formed from a flash memory or the like, and controls the overall operation of electronic cassette 10.

Further, cassette controller 58 is connected to wireless communications unit 60. Wireless communications unit 60 is compatible with the local area network (LAN) standard specified, for example, by the Institute of Electrical and Electronics Engineers (IEEE) 802.11a/b/g/n and controls transmission of various kinds of information by wireless communication with an external device. Cassette controller 58 is able to engage in wireless communication with an external device that performs control or management of radiographic imaging (for example, a console that operates equipment such as a radiation generator or a server connected to a hospital internal network) via wireless communications unit 60, and can transmit and receive various kinds of information to and from a console. Wireless communications unit 60 is one example of a communications section as recited in claim 6.

Cassette controller 58 stores various kinds of information received from the console via wireless communications unit 60 such as information on imaging conditions and patient information and performs driving of radiation detection panel 20 based on the information on imaging conditions and readout of the charge from radiation detection panel 20. Further, display portion 82 and operation portion 84 are also connected to cassette controller 58 and cassette controller 58 stores the content of operation performed via operation portion 84 by an operator such as an imaging technician and performs communication of information with the exterior based on the stored information and/or processes display or the like of various kinds of information at display portion 82.

Further, power source section 70 supplies electrical power to each of the circuits and elements described above (display portion 82, operation portion 84, gate line driver 52, signal processor 54, image memory 56, wireless communications unit 60, and the microcomputer that functions as cassette controller 58). Note that wiring connecting power source section 70 with each of the circuits and elements is omitted from FIG. 5. Power source section 70 incorporates a battery (secondary cell) in order to ensure that electronic cassette 10 is portable and a charged battery is used as the source of electrical power supply to each of the circuits and elements.

Next, the mechanism of the first exemplary embodiment is explained. In a state in which, as shown in FIG. 1A, panel unit 12 and control unit 14 are stacked one on the other and the entire surface of irradiation surface 18 of panel unit 12 is covered by control unit 14 in the storage state and stopper 80 is rotated to the holding position as shown in FIG. 1A, electronic cassette 10 can be held by handle portion 72 and carried. In this way, in electronic cassette 10 according to the first exemplary embodiment, since surface 18 of panel unit 12 is protected by control unit 14 which covers the entire irradiation surface 18 in the storage state, damage to irradiation surface 18 during transportation of electronic cassette 10 is prevented.

Further, when electronic cassette 10 has been carried to a position at which radiographic image capture is possible, electronic cassette 10 is first placed by an operator on a base platform such that panel unit 12 is at the lower side and display/operation surface 14A of control unit 14 faces upward. Then, as shown in FIGS. 1B and 1C, stopper 80 is rotated to the release position, after which the side surfaces or the like of control unit 14 are held and control unit 14 is moved with pin 74 as the approximate center of rotation such that display/operation surface 14A remains in an approximately horizontal state. In conjunction with this movement, the pair of connection rods 16 are rotated relative to panel unit 12 and control unit 14, electronic cassette 10 transitions from the storage state shown in FIG. 1A to the deployed state shown in FIG. 1C via the intermediate state shown in FIG. 1B. As a result, while irradiation surface 18 of panel unit 12 is exposed, control unit 14 is maintained in a state in which display/operation surface 14A faces upward.

When electronic cassette 10 is in the deployed state, the operator sends a command via operation portion 84 for transmission of information on imaging conditions and patient information from an external device. Cassette controller 58 receives information on imaging conditions and patient information from an external device via wireless communications unit 60 and displays information that can be used to identify the patient (such as the name or ID of the patient) at display portion 82. The imaging technician or other operator checks the name of the actual subject and, for example, by verifying the checked name against the displayed name of the patient at display portion 82, it is possible to ensure that there are no errors in terms of the imaging subject.

Further, the information displayed at display portion 82 is not limited to patient information and, for example, the imaging technician or other operator is made aware of the relevant imaging conditions according to imaging condition information displayed at display portion 82, Alternatively, by displaying data acquired from an external device regarding previous radiographic images of the same region of the same subject, the imaging technician or other operator can be made aware of the scope of previous imaging. Further, sample images corresponding to the imaging target region or imaging guidance may be displayed at display portion 82.

Further, since display/operation surface 14A of control unit 14 is mounted so as to face upwards when electronic cassette 10 is in the storage state, commands for transmission of various kinds of information by an operator, receipt of various kinds of information from an external device, and display of information related to patients at display portion 82 can be performed in the storage state before putting electronic cassette 10 in the deployed state.

Figure 6A:
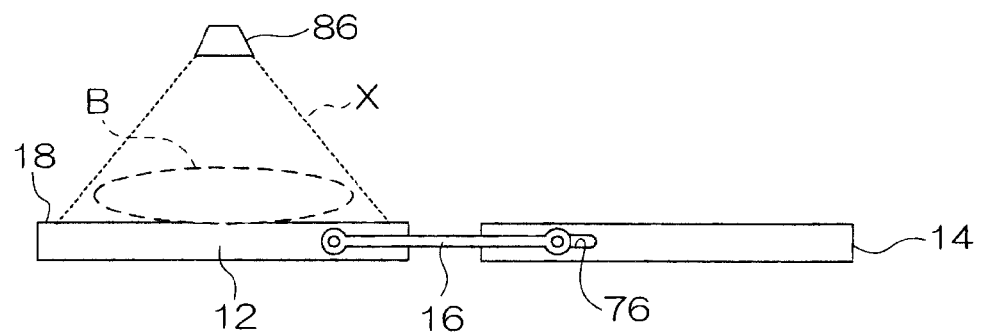
FIGS. 6A-6C are lateral views each showing an example of the arrangement of the respective units of the electronic cassette at the time of imaging.

When confirmation of the subject by the imaging technician has been completed, electronic cassette 10 is disposed at an interval from radiation generator 86, as shown in FIG. 6A and imaging target region B of the subject is disposed on irradiation surface 18 of panel unit 12. Radiation generator 86 emits radiation in an amount corresponding, for example, to imaging conditions provided in advance. X-rays emitted from radiation generator 86 transmit through each part of imaging target region B and irradiate irradiation surface 18 after the dose thereof has changed in accordance with the radiation transmittance of each part of imaging target region B. Charge corresponding to the irradiated dose of x-rays at positions corresponding to the surface of irradiation surface 18 are collected and accumulated at each of the charge collection electrodes 34 in radiation detection panel 20 housed in electronic cassette 10.

After irradiation of x-rays is complete, cassette controller 58 controls gate line driver 52, outputs ON signals from gate line driver 52 to each one line of the gate wires 40 and turns on each of the switching elements 24 connected to the respective gate wires 40 at one line after the other. As a result, the charge accumulated at the respective charge collection electrodes 34 flows as an electrical signal to each of the data wires 42 at one line after the other. The electrical signal (radiographic detection signal) that has flowed to the respective data wires 42 is input to signal processor 54, converted to digital image data (radiographic image data), and stored at image memory 56. When imaging is complete, cassette controller 58 displays a radiographic image representing the radiographic image data stored at image memory 56 or sends the radiographic image data to an external device such as a console. Further, while the above operation is for imaging of a still image, imaging for a moving image may be performed by continuous image capture.

In this way, imaging is performed after electronic cassette 10 has been put into the deployed state in which side surfaces of panel unit 12 and control unit 14 face each other with a space therebetween; namely, thermal coupling between panel unit 12 and control unit 14 is significantly lower than in the storage state. As a result, an increase in the temperature of radiation detection panel 20 caused by transmission of heat generated at control section 50 or power source section 70 inside control unit 14 can be suppressed without providing a cooling means or the like inside panel unit 12. Accordingly, changes in the properties of radiation detection panel 20 are suppressed and the image quality of captured radiographic images becomes consistent and, in addition, deterioration of radiation detection panel 20 is suppressed and the durability of radiation detection panel 20 is improved. In particular, when scintillator layer 28 is formed from a material including CsI, which has a high rate of change in sensitivity to radiation relative to temperature change, since it is possible to suppress increases in the temperature of radiation detection panel 20 as described above, it is possible to obtain a remarkable effect of consistency of image quality, whereby, even when capturing moving images, deterioration in the visibility of moving images and affection to diagnoses based on moving images are prevented. Further, as increase in the surface temperature of panel unit 12 can be suppressed, a subject can be prevented from feeling discomfort due to contacting panel unit 12 at the time of imaging.

Figure 6B:
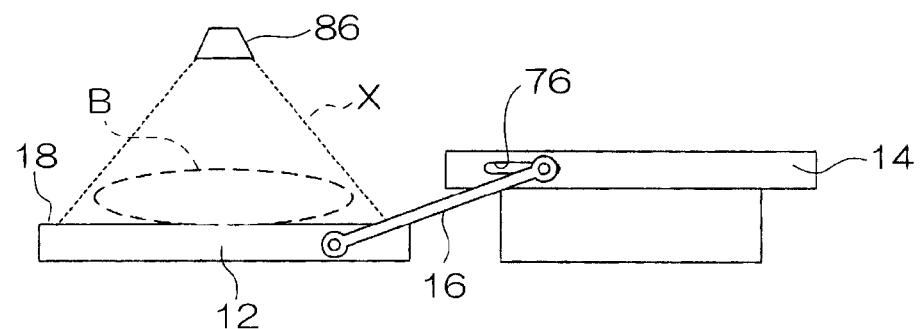
Figure 6C:
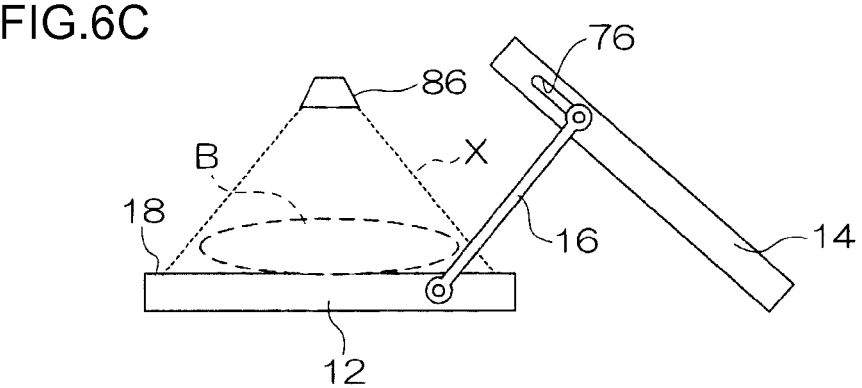

Further, electronic cassette 10 according to the first exemplary embodiment is configured such that panel unit 12 and control unit 14 are connected via connection rods 16, and connection rods 16 are rotatable relative to panel unit 12 and control unit 14. Control unit 14 has a high degree of freedom in terms of position and attitude at the time of image capture. Control unit 14 can be placed in the same plane as panel unit 12 at the time of image capture as shown in FIG. 6A, it is also possible to change the position and attitude of control unit 14 as necessary by, for example, placing control unit 14 in a plane at a different height from panel unit 12 as shown in FIG. 6B or disposing control unit 14 at an angle relative to panel unit 12 as shown in FIG. 6C.

Further, since it is sufficient for electronic cassette 10 to be put in the deployed state and for only panel unit 12 to be disposed at imaging target region B when performing image capture, the thickness of the portion to be disposed at imaging target region B is reduced and can easily inserted beneath a subject in a recumbent position. Further, because control unit 14 is spatially removed from imaging target region B, it easily ensures that air is not blown directly onto a subject even when, for example, control unit 14 is subjected to forced cooling by an air-cooling fan.

Further, since the surface area of electronic cassette 10 is increased by putting electronic cassette 10 in the deployed state when performing image capture, the heat dissipation effect is increased. Since the amount of heat generated at control unit 14 is particularly increased when capturing a moving image, a larger surface area is preferable in view of heat dissipation. Further, a configuration may be adopted in which the heat dissipation effect is further raised by giving the surface of control unit 14 a non-planar shape and thus increasing the surface area thereof. The non-planar shape might be any shape such as a corrugated or a hemispheric shape.

Further, electronic cassette 10 according to the first exemplary embodiment can be reduced in weight and thickness because a heavy metal for exposure prevention is not necessary to be incorporated in control unit 14 as control unit 14 can be disposed outside of the x-ray irradiation region during image capture. Further, since wireless communications unit 60 is provided inside control unit 14, which is distanced from the subject in the deployed state, the antenna for wireless communication is also disposed at a position distanced from the subject, there is the advantage that the likelihood of electromagnetic interference is reduced.

Second Exemplary Embodiment

Next, the second exemplary embodiment of the present invention is explained. Further, parts that are the same as the first exemplary embodiment are given the same reference numerals and explanation thereof is omitted. FIGS. 7 and 8 show electronic cassette 90 according to the second exemplary embodiment.

Electronic cassette 90 according to the second exemplary embodiment has radiation detection panel 20 incorporated in panel unit 12 as in electronic cassette 10 explained in the first exemplary embodiment; however, in radiation detection panel 20, TFT substrate 26, planarization layer 38, and adhesive layer 39 shown in FIG. 3 are formed from materials that allow transmittance of radiation. In addition to a case in which radiation is irradiated from the side of scintillator layer 28 as explained in the first exemplary embodiment, in radiation detection panel 20, detection of incident radiation that is; conversion of incident radiation to light at scintillator layer 28, generation of charge at photoconductive layers 30, and collection of generated charge at charge collection electrodes 34; is possible even when radiation is irradiated from the side of TFT substrate 26. Therefore, in electronic cassette 90 according to the second exemplary embodiment, the reverse surface to irradiation surface 18 (the surface positioned at the TFT substrate 26 side of radiation detection panel 20) is also used as a surface onto which radiation is irradiated, and the front and rear irradiation surfaces may be used selectively when capturing radiographic images.

Further, among the front and rear irradiation surfaces, with respect to the irradiation surface at the side of scintillator layer 28 (referred to below as the "front irradiation surface" for convenience), because no TFT substrate 26 or the like is present between the irradiation surface and scintillator layer 28 and because the radiation dose incident on scintillator layer 28 is larger than when the irradiation surface at the side of TFT substrate 26 (referred to below as the "rear irradiation surface" for convenience) is used, the front irradiation surface is used for normal imaging. On the other hand, with respect to the rear irradiation surface, although the radiation dose incident on scintillator layer 28 is smaller than when the front irradiation surface is used, since conversion from radiation to light takes place at a portion of scintillator layer 28 that is closer to photoconductive layers 30 in a thickness direction, the distance between the portion of scintillator layer 28 and photoconductive layers 30 is reduced and the level of diffusion of light incident on photoconductive layers 30 is also reduced. As a result, a higher definition radiographic image is obtained. Therefore, when the radiation dose irradiated onto electronic cassette 90 is relatively high and when a high definition radiographic image is required, imaging is performed using the rear irradiation surface.

Further, since the front and rear irradiation surfaces of electronic cassette 90 can be used selectively, long holes 76 provided in the pair of side surfaces of control unit 14 are made longer than in electronic cassette 10 explained in the first exemplary embodiment as shown in FIGS. 7 and 8 in order to enable control unit 14 to be inverted relative to panel unit 12. In addition, the length of long holes 76 of electronic cassette 90 is determined such that control unit 14 is able to rotate around an axis that is substantially orthogonal to the pair of side surfaces of control unit 14 (the axis of pin 78) without being impeded by panel unit 12.

Figure 7A:
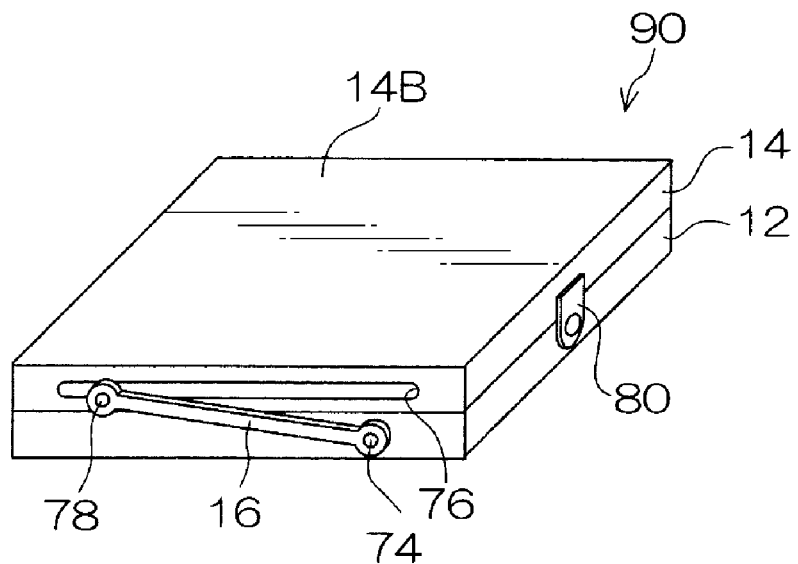
FIGS. 7A-7D are perspective views showing the outer appearance of an electronic cassette according to a second exemplary embodiment.

Next, the mechanism of the second exemplary embodiment is explained. As shown in FIG. 7A, electronic cassette 90 is in a storage state in which control unit 14 is stacked on panel unit 12 and display/operation surface 14A of control unit 14 is in contact with either the front or rear irradiation surface of panel unit 12. In this state, and also with stopper 80 rotated to the holding position shown in FIG. 7A, handle portion 72 can be held and electronic cassette 90 carried. The entire surface of display/operation surface 14A of control unit 14 is covered and protected by panel unit 12 and reverse surface 14B of display/operation surface 14A is exposed to the outside in the storage state, and damage such as scratching of display/operation surface 14A or breakage of display portion 82 or operation portion 84 of control unit 14 is prevented.

In addition, in electronic cassette 90 in the above storage state, since, of the front and rear irradiation surfaces of panel unit 12, the irradiation surface that is not in contact with display/operation surface 14A of control unit 14 is exposed to the outside, damage might be caused on the exposed irradiation surface. Accordingly, the exposed irradiation surface to the outside in the storage state may, for example, be coated with a material that transmits radiation in order to prevent damage. Alternatively, damage to the exposed irradiation surface may be prevented by further accommodating electronic cassette 90 in a protective case or the like when carrying electronic cassette 90 in the storage state.

Figure 7B:
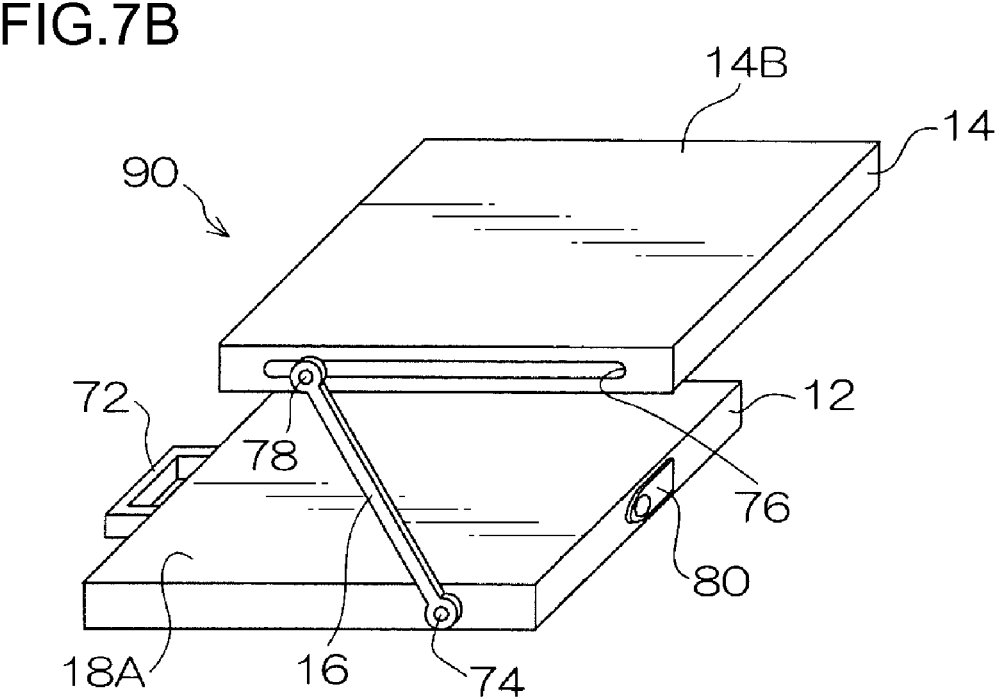
Figure 7C:
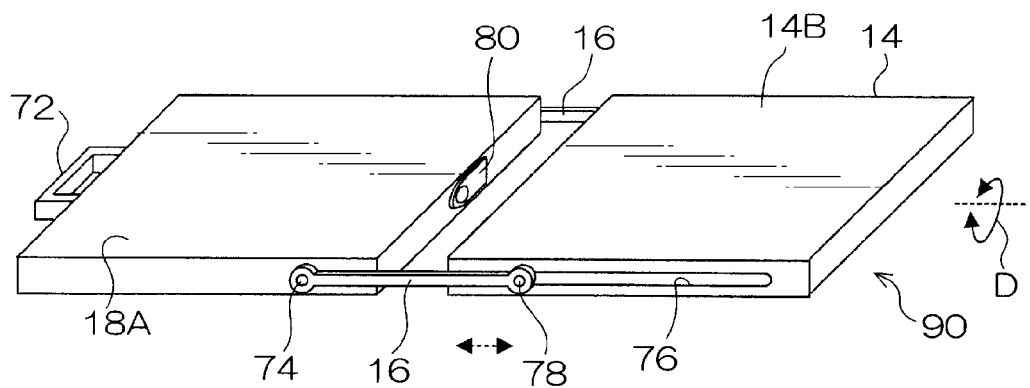
Figure 7D:
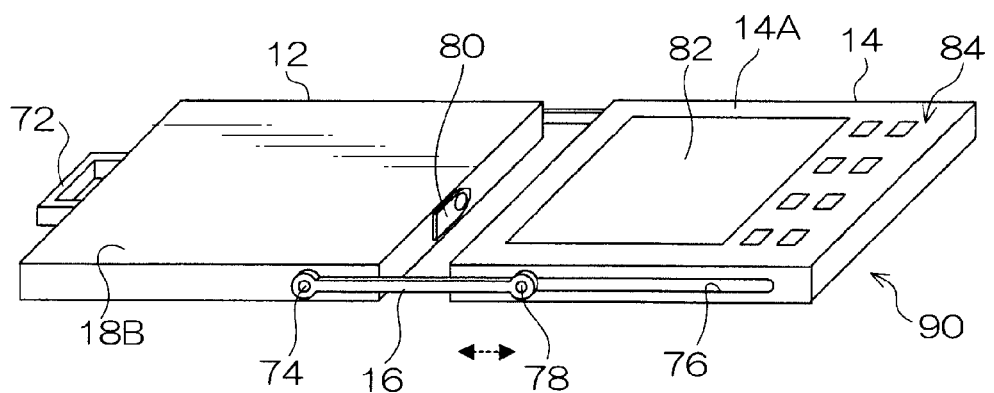

Further, when electronic cassette 90 is carried to a position at which radiographic image capture is possible, electronic cassette 90 is first placed by an operator on a platform with panel unit 12 at the lower side thereof, then, after stopper 80 is rotated to the release position shown in FIGS. 7B-7D, the side surfaces of whichever of panel unit 12 and control unit 14 is positioned uppermost (control unit 14 in FIG. 7) are held and said unit is moved with pin 74 or pin 78 as the approximate centers of rotation while keeping the upper surface of the unit (reverse surface 14B of control unit 14 in FIG. 7) in an approximately planar state. The pair of connection rods 16 are rotated relative to panel unit 12 and control unit 14 in conjunction with this movement, a transition is effected from the storage state shown in FIG. 7A to the deployed state shown in FIG. 7C via the intermediate state shown in FIG. 7B.

Figure 8A:
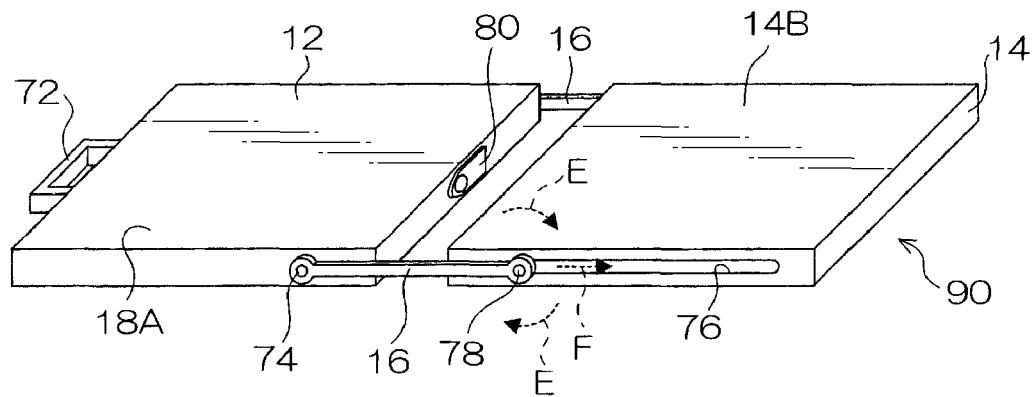
FIGS. 8A-8D are perspective views showing the outer appearance of an electronic cassette according to a second exemplary embodiment.
Figure 8B:
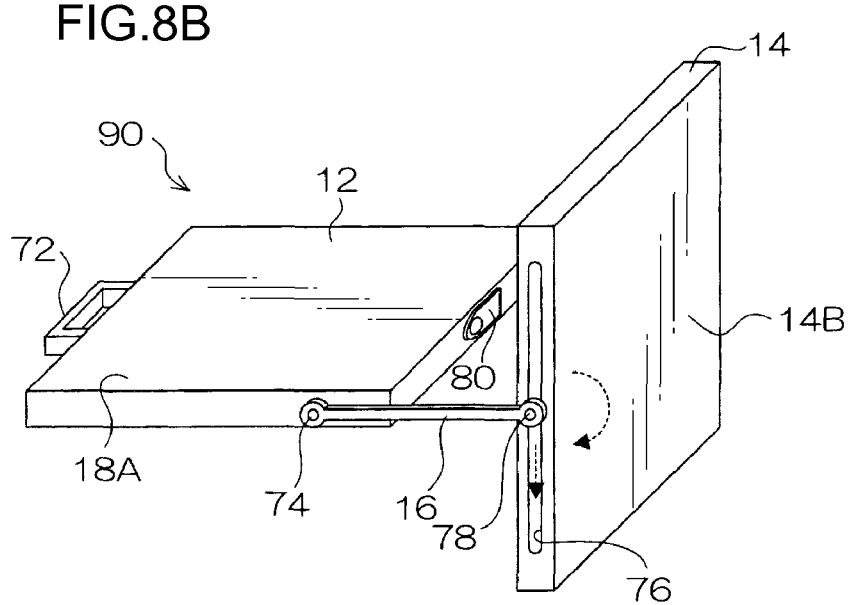

When, of the front and rear irradiation surfaces of panel unit 12, the irradiation surface exposed to the outside in the storage state is to be used in imaging, in other word, the reverse side irradiation surface 18B to the irradiation surface 18A in FIGS. 7B and 8A is to be used for imaging, the whole of electronic cassette 90 in the deployed state is integrally turned upside-down in the direction of Arrow D in FIG. 7C. As a result, as shown in FIG. 7D, the irradiation surface 18B of panel unit 12 faces upward and display/operation surface 14A of control unit 14 is also faces upward and confirmation of the subject as explained in the first exemplary embodiment and radiographic image capture can be performed.

In addition, the sequence of operations in order to use irradiation surface 18B is not limited to the above explanation. This can be achieved by, for example, first placing electronic cassette 90 on a platform with panel unit 12 at the upper side thereof while irradiation surface 18B is exposed to the outside then, after stopper 80 is rotated to the release position, holding the side surfaces of panel unit 12 and moving panel unit 12 with pin 74 and pin 78 as the approximate centers of rotation while keeping the upper surface of panel unit 12 in an approximately planar state. In this case, electronic cassette 90 is put into the state shown in FIG. 7D when electronic cassette 90 is put into the deployed state. Irradiation surface 18B, which is to be used in imaging, faces upward and display/operation surface 14A of control unit 14 also faces upward.

Further, when, the irradiation surface 18A that was in contact with display/operation surface 14A of control unit 14 in the storage state is to be used, an operator performs such that only control unit 14 is rotated in the direction of Arrow E shown in FIG. 8A with pin 78 as the approximate center of rotation. Pin 78 and the end portions of the pair of connection rods 16 attached to pin 78 are moved inside long holes 76 in the direction of Arrow F in FIG. 8A. As a result, from the state shown in FIG. 8A, and via the state shown in FIG. 8B, irradiation surface 18A of panel unit 12 faces upward and display/operation surface 14A of control unit 14 also faces upward as shown in FIG. 8C and confirmation of the subject and radiographic image capture can be performed.

Further, when the portion of a subject's leg from the knee downward is to be imaged, image capture is commonly performed in a state that the subject is seated on a bed in a posture with one knee raised and the subject holds the electronic cassette such that the irradiation surface is approximately facing the raised knee in a vertical direction. In such cases, there is a possibility that the subject's hand will suffer a certain amount of exposure. However, with electronic cassette 90 according to the second exemplary embodiment, from the state shown in FIG. 8B, after inverting the front and rear of control unit 14 such that reverse surface 14B of control unit 14 faces panel unit 12, the whole of electronic cassette 90 is rotated approximately 90° as shown in FIG. 8D, irradiation surface 18A of panel unit 12 approximately faces the knee that has been raised in a vertical direction. Further, panel unit 12 is prevented from overturning by control unit 14.

As a result, even when imaging is performed with irradiation surface 18A of electronic cassette 90 disposed vertically, imaging can be performed simply by disposing imaging target region B of the subject in front of irradiation surface 18A without holding electronic cassette 90 by the subject's hand. Further, since display/operation surface 14A of control unit 14 is facing the outer side (the opposite side to panel unit 12) in the state shown in FIG. 8D, the imaging technician or other operator can operate operation portion 84 and visually verify information displayed at display portion 82.

Figure 8C:
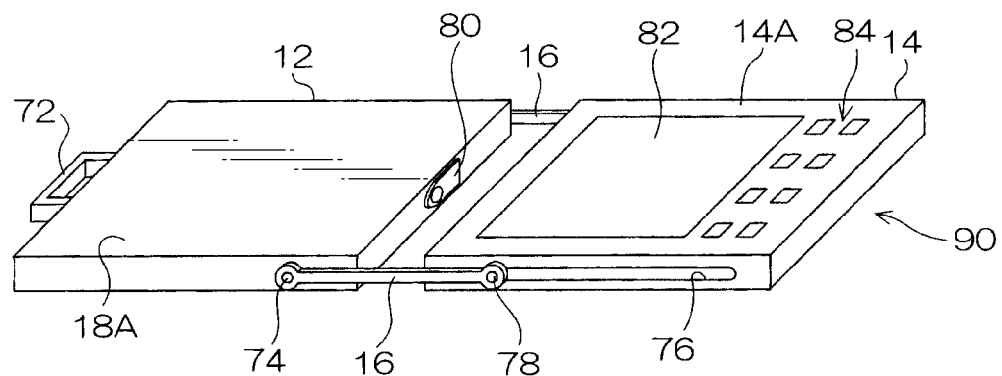
Figure 8D:
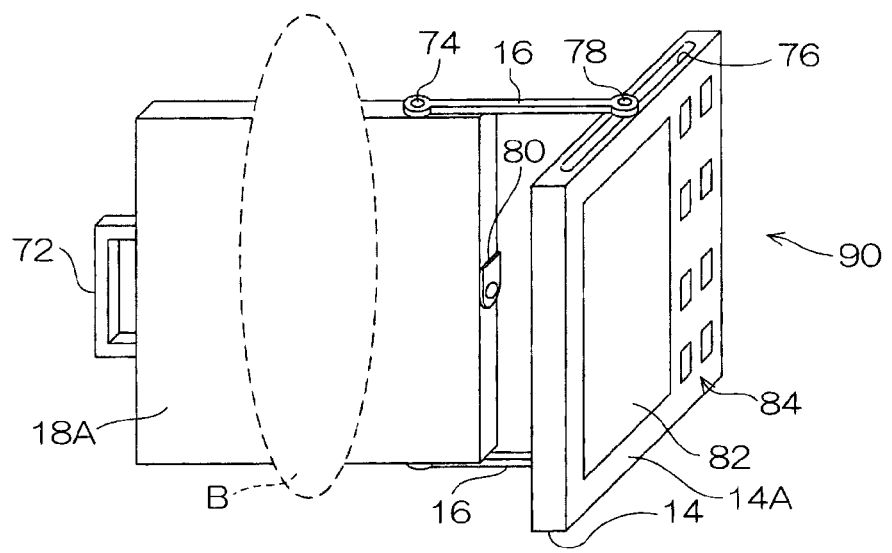

In this way, in electronic cassette 90 according to the second exemplary embodiment, whichever of the front or rear irradiation surfaces of panel unit 12 is used to perform radiographic image capture, the respective side surfaces of panel unit 12 and control unit 14 face each other across a gap, as shown in FIGS. 7D and 8C. Accordingly, because imaging can be performed in a state in which thermal coupling between panel unit 12 and control unit 14 is significantly lower than in the storage state, an increase in the temperature of radiation detection panel 20 caused by transmission of heat generated, for example, at control section 50 or power source section 70 inside control unit 14 can be suppressed without providing a cooling means or the like inside panel unit 12. As a result, changes in the properties of radiation detection panel 20 are suppressed and the image quality of captured radiographic images becomes consistent and, deterioration of radiation detection panel 20 is suppressed and the durability of radiation detection panel 20 is improved. Further, by suppressing an increase in the surface temperature of panel unit 12, a subject contacting panel unit 12 at the time of imaging can be prevented from feeling discomfort.

Further, similarly to electronic cassette 10 explained in the first exemplary embodiment, in electronic cassette 90 according to the second exemplary embodiment, control unit 14 has a high degree of freedom in terms of position and attitude and, as shown in FIGS. 6A-6C, the position and attitude of control unit 14 can be changed as necessary at the time of image capture. Additionally, since either of the front and rear irradiation surfaces of panel unit 12 can be used for radiographic image capture, the degree of freedom of radiographic image capture is improved. Further, whichever of the front or rear irradiation surfaces of panel unit 12 is used to perform radiographic image capture, control unit 14 can be put in a state in which display/operation surface 14A faces upwards as shown in FIGS. 7D and 8C and confirmation of the subject, radiographic image capture and the like can be performed with the same procedure.

Similarly to electronic cassette 10 in the first exemplary embodiment, since it is sufficient for electronic cassette 90 to be put in the deployed state and for only panel unit 12 to be disposed at imaging target region B when performing image capture, the thickness of the portion to be disposed at imaging target region B is reduced and, can easily inserted beneath a subject in a recumbent position. Further, in electronic cassette 90, similarly to electronic cassette 10 in the first exemplary embodiment, because control unit 14 is spatially removed from imaging target region B, it is possible to easily ensure that air is not blown directly onto a subject even when control unit 14 is subjected to forced cooling by an air-cooling fan.

Since the surface area of electronic cassette 90 is increased by putting electronic cassette 90 in the deployed state when performing image capture, the heat dissipation effect is increased. Since the amount of heat generated at control unit 14 is particularly increased when capturing a moving image, a larger surface area is preferable in view of heat dissipation.

Further, electronic cassette 90 can be reduced in weight and thickness because a heavy metal for exposure prevention in control unit 14 is not necessary as control unit 14 can be disposed outside of the x-ray irradiation region during image capture. Since wireless communications unit 60 is provided inside control unit 14, which is distanced from the subject in the deployed state and the antenna for wireless communication is also disposed at a position distanced from the subject, there is the advantage that the likelihood of electromagnetic interference is reduced.

Figure 9:
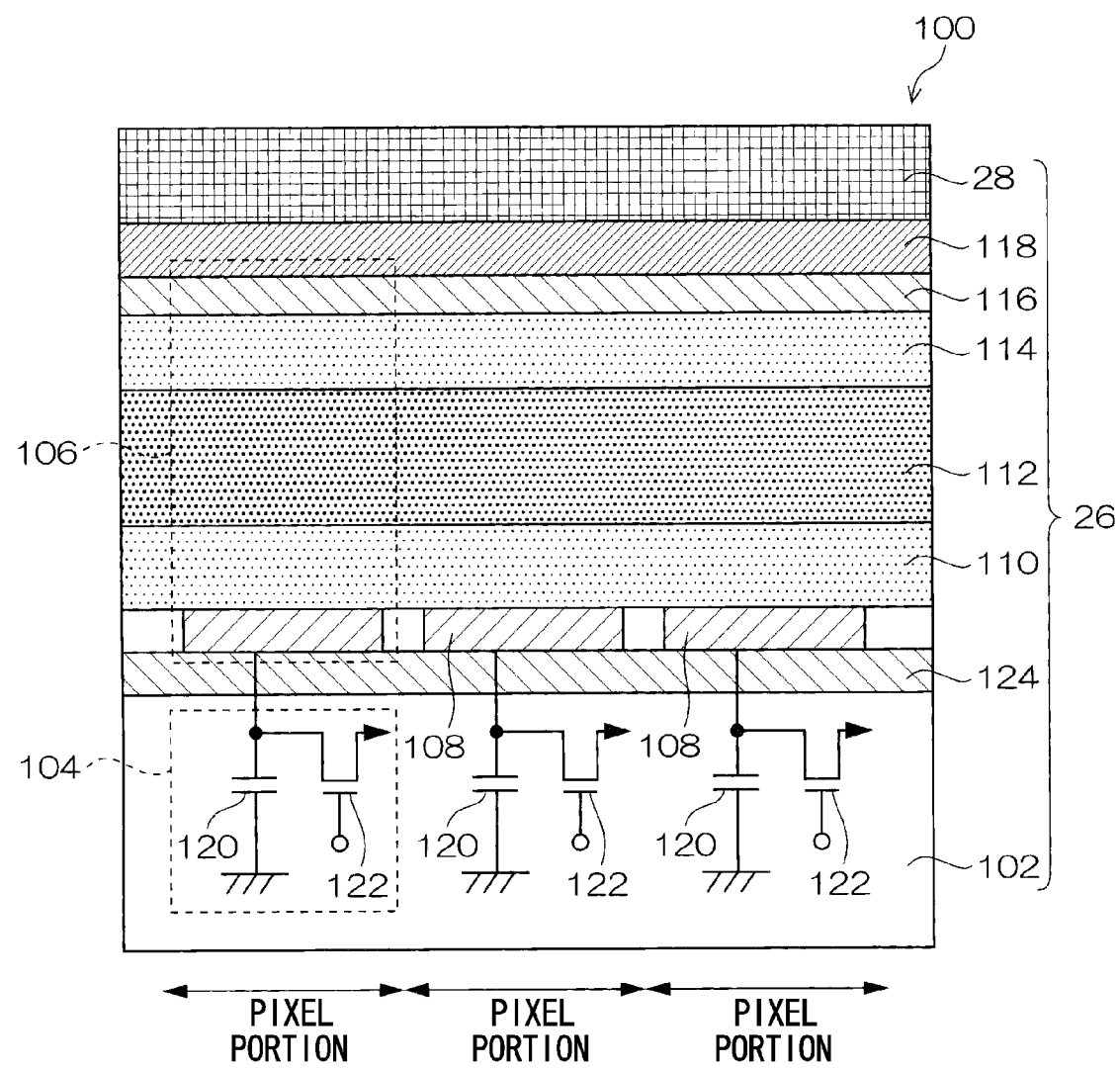
FIG. 9 is a sectional view showing a variant example of a schematic configuration of a radiation detection panel.

Next, an alternative configuration of a radiation detection panel that can be used in electronic cassette 10 in the first exemplary embodiment and electronic cassette 90 in the second exemplary embodiment instead of radiation detection panel 20 is explained with reference to FIG. 9. In radiation detection panel 100 shown in FIG. 9, TFT substrate 26 has signal output portion 104 and sensor portion 106 provided in this order on insulating substrate 102 and scintillator layer 28 is layered on the upper layer of TFT substrate 26 and, at TFT substrate 26, plural pixel portions equipped with signal output portion 104 and sensor portion 106 are disposed in a matrix on substrate 102.

Sensor portion 106 has upper portion electrode 116, lower portion electrode 108, and photoelectric conversion film 112 disposed between electrodes 116 and 108, and photoelectric conversion film 112 is formed from an organic photoelectric conversion material that absorbs light emitted from scintillator layer 28 and generates electrical charge. Further, separately to signal output portion 104, sensor portion 106 is configured to detect the amount of radiation irradiated at radiation detection panel 100 by detecting the amount of light emitted from scintillator layer 28, and the result of the amount of radiation detected by sensor portion 106 is read out via a signal processor (not shown) connected to electrodes 116 and 108, and used, for example, to determine the timing of commencement or termination of irradiation to radiation detection panel 100 or to calculate an cumulative value of the amount of radiation irradiated at radiation detection panel 100.

Upper portion electrode 116 is preferably configured from an electrically conductive material that is transparent at least relative to the wavelength of the light emitted from scintillator layer 28 in view of the fact that the light emitted from scintillator layer 28 needs to be incident on photoelectric conversion film 112 and, specifically, it is preferable to use a transparent conducting oxide (TCO) having high transmittance with respect to visible light and a low resistance value. Further, while a metal thin film of Au or the like may be used as upper portion electrode 116, a TCO is preferable because the resistance value tends to increase in metal thin film when configured so as to obtain a light transmittance of 90% or higher. It is preferable to use ITO, IZO, AZO, FTO, $SnO_2$, $TiO_2$ or $ZnO_2$, and ITO is the most preferable in view of ease of processing, low resistance and transparency. Further, upper portion electrode 116 may be configured such that a single sheet thereof is used for all the pixels or it may be divided into separate portions for each pixel.

Photoelectric conversion film 112 includes an organic photoelectric conversion material and absorbs light emitted from scintillator layer 28 and generates electrical charge corresponding to the absorbed light. Photoelectric conversion film 112, containing an organic photoelectric conversion material, has a sharp absorption spectrum in the visible light region and almost no electromagnetic waves other than the light emitted from scintillator layer 28 are absorbed by photoelectric conversion film 112, such that noise generated by absorption of radiation such as x-rays at photoelectric conversion film 112 can be effectively suppressed.

The organic photoelectric conversion material used in photoelectric conversion film 112 preferably has an absorption peak wavelength that is close to the light emission peak wavelength of scintillator layer 28 so as to enable the most efficient absorption of light emitted from scintillator layer 28. While the absorption peak wavelength of the organic photoelectric conversion material ideally matches the light emission peak wavelength of scintillator layer 28, it is possible for light emitted from scintillator layer 28 to be sufficiently absorbed as long as any difference between the two peak wave lengths is small. Specifically, the difference between the absorption peak wavelength of the organic photoelectric conversion material and the light emission peak wavelength of scintillator layer 28 is preferably 10 nm or less and more preferably 5 nm or less.

Examples of an organic photoelectric conversion material that can satisfy this condition include quinacridone organic compounds and phthalocyanine organic compounds. Since, the absorption peak wavelength of quinacridone in the visible region is 560 nm, when quinacridone is used as the organic photoelectric conversion material and CsI (Tl) is used as the material for scintillator layer 28, the above difference in peak wavelength can be brought to within 5 nm and the amount of electrical charge generated at photoelectric conversion film 112 can be almost maximized.

Photoelectric conversion films 112 that can be applied to radiation detection panel 100 are explained in detail. The electromagnetic wave absorption/photoelectric conversion region of radiation detection panel 100 is provided as an organic layer including the pair of electrodes 116 and 108, and photoelectric conversion film 112 disposed between electrodes 116 and 108. In more detail, this organic layer can be formed by layering a region for absorption of electromagnetic waves, a photoelectric conversion region, an electron transport region, a hole transport region, an electron blocking region, a hole blocking region, a crystallization prevention region, electrodes, and a region for improvement of contact between layers, or by mixing these regions together.

The organic layer preferably includes an organic p-type compound or an organic n-type compound. An organic p-type semiconductor (compound) is a donor-type organic semiconductor (compound) represented mainly by hole transporting organic compounds, and has properties that facilitate electron donation. To be more specific, it is an organic compound having the smaller ionized potential when two organic materials are used in contact with each other. Accordingly, any organic compound that has electron-donating properties may be used as the donor-type organic compound. An organic n-type semiconductor (compound) is an acceptor-type organic semiconductor (compound) represented mainly by electron-transporting organic compounds, and has properties that facilitate electron acceptance. To be more specific, it is an organic compound having the larger electron affinity when two organic compounds are used in contact with each other. Accordingly, any organic compound that has electron-accepting properties may be used as the acceptor-type organic compound.

Since materials that can be applied as the organic p-type semiconductor and the organic n-type semiconductor and the configuration of photoelectric conversion film 112 are described in detail in JP-A No. 2009-32854, explanation thereof is not provided here.

Sensor portion 106 configuring each pixel portion may at least include lower portion electrode 108, photoelectric conversion film 112 and upper portion electrode 116, but preferably also includes either electron blocking film 110 or hole blocking film 114, and more preferably also includes both, in order to suppress increases in dark current.

Electron blocking film 110 may be provided between lower portion electrode 108 and photoelectric conversion film 112, whereby it is possible to prevent electrons from being injected from lower portion electrode 108 to photoelectric conversion film 112 and to prevent increases in dark current when bias voltage is applied between lower portion electrode 108 and upper portion electrode 116. An electron-donating organic material may be used in electron blocking film 110. The material actually used in electron blocking film 110 should be selected in view of the material of the adjacent electrode and the material of the adjacent photoelectric conversion film 112, and is preferably a material that has an electron affinity (Ea) that is at least 1.3 eV larger than the work function (Wf) of the material of the adjacent electrode and an ionized potential (Ip) that is the same as or smaller than the Ip of the material of the adjacent photoelectric conversion film 112. Since materials that can be applied as the electron-donating organic material are described in detail in JP-A No. 2009-32854, explanation thereof is not provided here.

The thickness of electron blocking film 110 is preferably from 10 nm to 200 nm, more preferably from 30 nm to 150 nm, and particularly preferably from 50 nm to 100 nm, in order to achieve a reliable dark current suppression effect and also to prevent reduction in the photoelectric conversion rate of sensor portion 106.

Hole blocking film 114 may be provided between photoelectric conversion film 112 and upper portion electrode 116, whereby it is possible to prevent holes from being injected from upper portion electrode 116 to photoelectric conversion film 112 and to prevent increases in dark current when bias voltage is applied between lower portion electrode 108 and upper portion electrode 116. An electron-accepting organic material may be used as hole blocking film 114. The material actually used in hole blocking film 114 should be selected in view of the material of the adjacent electrode and the material of the adjacent photoelectric conversion film 112, and is preferably a material that has an Ip that is at least 1.3 eV larger than the Wf of the material of the adjacent electrode and an Ea that is the same as or smaller than the Ea of the material of the adjacent photoelectric conversion film 112. Since materials that can be applied as the electron-accepting organic material are described in detail in JP-A No. 2009-32854, explanation thereof is not provided here.

The thickness of hole blocking film 114 is preferably from 10 nm to 200 nm, more preferably from 30 nm to 150 nm, and particularly preferably from 50 nm to 100 nm, in order to achieve a reliable dark current suppression effect and also to prevent reduction in the photoelectric conversion rate of sensor portion 106.

Further, when the bias voltage is set such that, among the charge generated at photoelectric conversion film 112, the holes move to upper portion electrode 116 and the electrons move to lower portion electrode 108, the positions of electron blocking film 110 and hole blocking film 114 may be reversed. Further, it is not necessary to provide both electron blocking film 110 and hole blocking film 114 as it is possible to achieve a certain level of dark current suppression effect by providing one or the other.

Signal output portion 104 is provided at substrate 102 below lower portion electrode 108 in each pixel and in correspondence with each lower portion electrode 108. Signal output portion 104 is formed from condenser 120 which accumulates charge that has moved to lower portion electrode 108, and field-effect TFT 122 (below, simply referred to as TFT 122) which converts charge accumulated at condenser 120 to an electrical signal and outputs the electrical signal. The region at which condenser 120 and TFT 122 are formed has a portion that overlaps with lower portion electrode 108 in plan view. Further, in order to minimize the surface area of the pixel portion of radiation detection panel 100, the region at which condenser 120 and TFT 122 are formed is preferably covered completely by lower portion electrode 108.

Condenser 120 is electrically connected to the corresponding lower portion electrode 108 via wiring of an electrically conductive material that passes through insulation film 124 provided between substrate 102 and lower portion electrode 108. As a result, the electrical charge collected at lower portion electrode 108 is moved to condenser 120.

Figure 10:
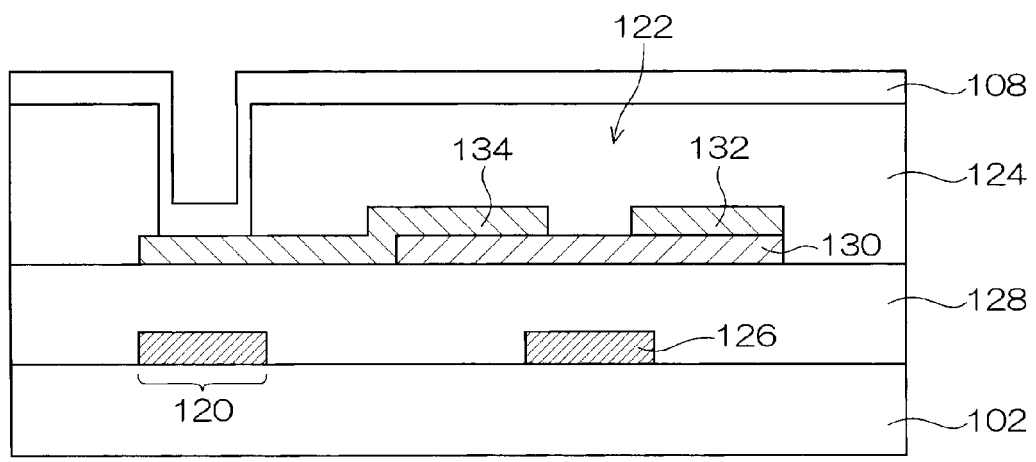
FIG. 10 is a sectional view showing a schematic configuration of a signal processing section of the radiation detection panel of FIG. 9.

As shown in FIG. 10, TFT 122 is formed by layering gate electrode 126, gate insulation film 128 and active layer (channel layer) 130 and, in addition, source electrode 132 and drain electrode 134 are formed on active layer 130 at a given interval from each other. Active layer 130 may be formed from any of amorphous silicon, an amorphous oxide, an organic semiconductor material, carbon nanotube or the like; however, the material that can be used to form active layer 130 is not limited thereto.

Preferable examples of an amorphous oxide that can be used to form active layer 130 include oxides that include at least one of In, Ga or Zn (for example, In—O oxides), while oxides that include at least two of In, Ga or Zn (for example, In—Zn—O oxides, In—Ga—O oxides or Ga—Zn—O oxides) are more preferable and oxides that include In, Ga and Zn are particularly preferable. Preferable examples of In—Ga—Zn—O amorphous oxides include amorphous oxides having a composition in a crystalline state represented by $InGaO_3(ZnO)_m$ (where m is a natural number lower than 6), and $InGaZnO_4$ is particularly preferable, Further, the amorphous oxide that can be used to form active layer 130 is not limited thereto.

Further, examples of an organic semiconductor material that can be used to form active layer 130 include phthalocyanine compounds, pentacene and vanadyl phthalocyanine, but are not limited thereto. Further, since the structure of the phthalocyanine compounds is described in detail in JP-A No. 2009-212389, explanation thereof is not provided here.

Further, if active layer 130 of TFT 122 is formed from any of an amorphous oxide, an organic semiconductor material or carbon nanotube, x-rays or other radiation is either not absorbed at all or, if absorbed, absorbed in extremely minute amounts, as a result of which generation of noise at signal output portion 104 can be effectively suppressed.

Further, when active layer 130 is formed from carbon nanotube, it is possible to increase the switching speed of TFT 122 and to reduce the degree of absorption of light in the visible range in TFT 122. In addition, when active layer 130 is formed from carbon nanotube, since the performance of TFT 122 is significantly impaired by the presence of even a minute amount of metallic impurities in active layer 130, it is necessary to use extremely high purity carbon nanotube that has been separated and extracted by centrifugal separation or the like, in the formation of active layer 130.

Any of the amorphous oxides, organic semiconductor materials or the like that can be used to form active layer 130 of TFT 122 and the organic photoelectric conversion material forming the photoelectric conversion film 112 can be formed into a film at low temperatures. Accordingly, substrate 102 is not limited to substrates having high heat resistance such as semiconductor substrates, quartz substrates or glass substrates, and flexible substrates such as plastic substrates, aramid, and bio-nanofiber can be used. Specifically, flexible substrates of, for example, polyesters such as polyethylene terephthalate, polybutylene phthalate and polyethylene naphthalate, polystyrene, polycarbonate, polyether sulfone, polyallylate, polyimide, polycyclo-olefin, norbornene resin or poly(chlorotrifluoroethylene) may be used. Use of this kind of plastic flexible substrate enables weight reduction, which is advantageous with respect to the carrying of an electronic cassette, for example.

In addition, since both a film formed from an organic photoelectric conversion material and a film formed from an organic semiconductor material have sufficient flexibility, in a configuration in which photoelectric conversion film 112 formed from an organic photoelectric conversion material is combined with TFT 122 in which active layer 130 is formed from an organic semiconductor material, the panel portion at which a patient's weight is applied as load does not necessarily need to be made rigid. However, when image capture is performed in a state in which panel unit 12 and control unit 14 are separated from each other as in the present exemplary embodiment, it is more effective to make panel unit 12 rigid.

Further, layers such as an insulation layer for preserving insulating properties, a gas barrier layer for preventing penetration of moisture or oxygen, and an undercoat layer for improving flatness or adherence to an electrode or the like, may be provided at substrate 102.

Since aramid can be subjected to processing at high temperatures of 200° C. or higher, a transparent electrode material containing aramid can be cured at high temperature and its resistance lowered, and aramid can be used in automatic implementation of a driver IC including reflow soldering. Further, since the thermal expansion coefficient of aramid is close to that of indium tin oxide (ITO) or glass substrate, there is little warpage or breakage after manufacture. Further, compared to glass substrate or the like, a thinner substrate can be formed with aramid. In addition, substrate 102 may be formed by layering ultra-thin glass substrate with aramid.

Bio-nanofiber is a composite of cellulose microfibril bundle (bacteria cellulose) produced by bacteria (acetic acid bacteria such as Acetobacter Xylinum) and a transparent resin. The cellulose microfibril bundle has a width of 50 nm which is a size approximately one-tenth of the wavelength of visible light, and has high strength, high elasticity, and low thermal expansion. By impregnating bacteria cellulose with a transparent resin such as acrylic resin or epoxy resin and curing the resultant, it is possible to obtain a bio-nanofiber with transmittance of approximately 90% at a wavelength of 500 nm that also includes 60-70% of fiber. Since bio-nanofiber has a low thermal expansion coefficient (3-7 ppm) comparable to that of silicon crystal, strength (460 MPa) comparable to steel, and high elasticity (30 GPa), and is also flexible, a thinner substrate 102 can be formed than glass substrate or the like.

Further, light emission is stronger at the upper surface side (the opposite side to TFT substrate 26) of scintillator layer 28 when radiation is irradiated from the front side at which scintillator layer 28 is formed in radiation detection panel 100 (front side irradiation), and light emission is stronger at the TFT substrate 26 side of scintillator layer 28 when radiation is irradiated from rear side that is the TFT substrate 26 side in radiation detection panel 100 (rear side irradiation) as radiation is incident on scintillator layer 28 after having transmitted through TFT substrate 26. Light made at scintillator layer 28 generates electrical charge at each sensor portion 106 provided at TFT substrate 26. As a result, the resolution of radiographic images obtained by image capture at radiation detection panel 100 is higher when radiation is irradiated from the rear side than when radiation is irradiated from the front side as light emission occurs closer to TFT substrate 26 in the former case.

Further, in radiation detection panel 100, photoelectric conversion film 112 is formed from an organic photoelectric conversion material and almost no radiation is absorbed at photoelectric conversion film 112. As a result, reduction in sensitivity to radiation can be prevented as the amount of radiation absorbed by photoelectric conversion film 112 is low even when radiation detection panel 100 is disposed such that radiation is transmitted through TFT substrate 26 due to rear side irradiation. In rear side irradiation, radiation arrives at scintillator layer 28 having transmitted through TFT substrate 26; however, when photoelectric conversion film 112 or TFT substrate 26 is formed from an organic photoelectric conversion material, almost no radiation is absorbed at photoelectric conversion film 112 and attenuation of the radiation can be kept to a minimum, such that radiation detection panel 100 is suitable for rear side irradiation.

Further, plastic resin, aramid, bio-nanofiber and the like all have low radiation absorption and when substrate 102 is formed from these materials as described above, the amount of radiation absorbed by substrate 102 is reduced, whereby reduction in sensitivity to radiation can be prevented even when radiation is transmitted through TFT substrate 26 by rear side irradiation.

Further, since the rigidity of radiation detection panel 100 as a whole is increased when substrate 102 is formed from plastic resin, aramid, bio-nanofiber or the like, which each have high rigidity, panel unit 12 can be formed with reduced thickness. Further, since radiation detection panel 100 as a whole has flexibility but substrate 102 is formed from the highly rigid plastic resin, aramid, bio-nanofiber or the like, the resistance of radiation detection panel 100 to impact is increased and radiation detection panel 100 becomes less susceptible to breakage when panel unit 12 or the like is subjected to impact.

While an aspect has been explained above in which, among the four side surfaces of panel unit 12, handle portion 72 is attached to a side surface between the pair of side surfaces to which the pair of connection rods 16 are attached via pin 74, the present invention is not limited to this. Handle portion 72 may also be attached to a side surface to which one of connection rods 16 is attached. This makes it possible to more reliably prevent a situation in which, while electronic cassette 10 or electronic cassette 90 in the storage state is being held by handle portion 72 and carried, electronic cassette 10 or electronic cassette 90 is unintentionally opened to the deployed state. Further, handle portion 72 is not limited to being attached to panel unit 12 and may be attached to control unit 14.

Further, while a configuration has been explained above in which long holes 76 are provided at the sides of control unit 14 and the end portions of connection rods 16 can move relative to control unit 14 along long holes 76, the present invention is not limited to this. Long holes may be provided at the sides of panel unit 12 and the end portions of connection rods 16 may be made movable relative to panel unit 12 along the long holes, or long holes may be provided at both control unit 14 and panel unit 12 and the respective end portions of connection rods 16 may be made movable relative to both control unit 14 and panel unit 12.

While wireless communications unit 60 performing wireless communication with an external device has been explained above as an example of the communications section recited in claim 6, the present invention is not limited to this. Instead of the above wireless communications unit, a fixed line communications unit performing wire communication with an external device may be provided. When a fixed line communications unit is provided at an electronic cassette in this way, a connector that is connected to a cable for performing wire communication is preferably provided at control unit 14. As a result, the connector and cable can be prevented from interfering with a subject and, in addition, when the electronic cassette is inserted under a subject, friction resistance or excessive load is not applied to the connector or the cable and connection defects such as loosening or disconnection can be forestalled.

In addition, in the first exemplary embodiment explained above, a configuration of electronic cassette 10 is explained in which radiation detection panel 20 shown in FIG. 3 is disposed inside panel unit 12 with an orientation such that the scintillator layer 28 side is closer to irradiation surface 18 than the TFT substrate 26 side thereof; however, the orientation of radiation detection panel 20 in electronic cassette 10 is not limited to the above description. Similar to the second exemplary embodiment, TFT substrate 26 (and planarization layer 38 and adhesive layer 39) of radiation detection panel 20 may be formed from materials through which radiation transmits, and a configuration may be adopted in which radiation detection panel 20 formed thus is disposed inside panel unit 12 with an orientation such that the TFT substrate 26 side is closer to irradiation surface 18 than the scintillator layer 28 side. Thereby, higher definition radiographic images can be obtained.

Figure 11:
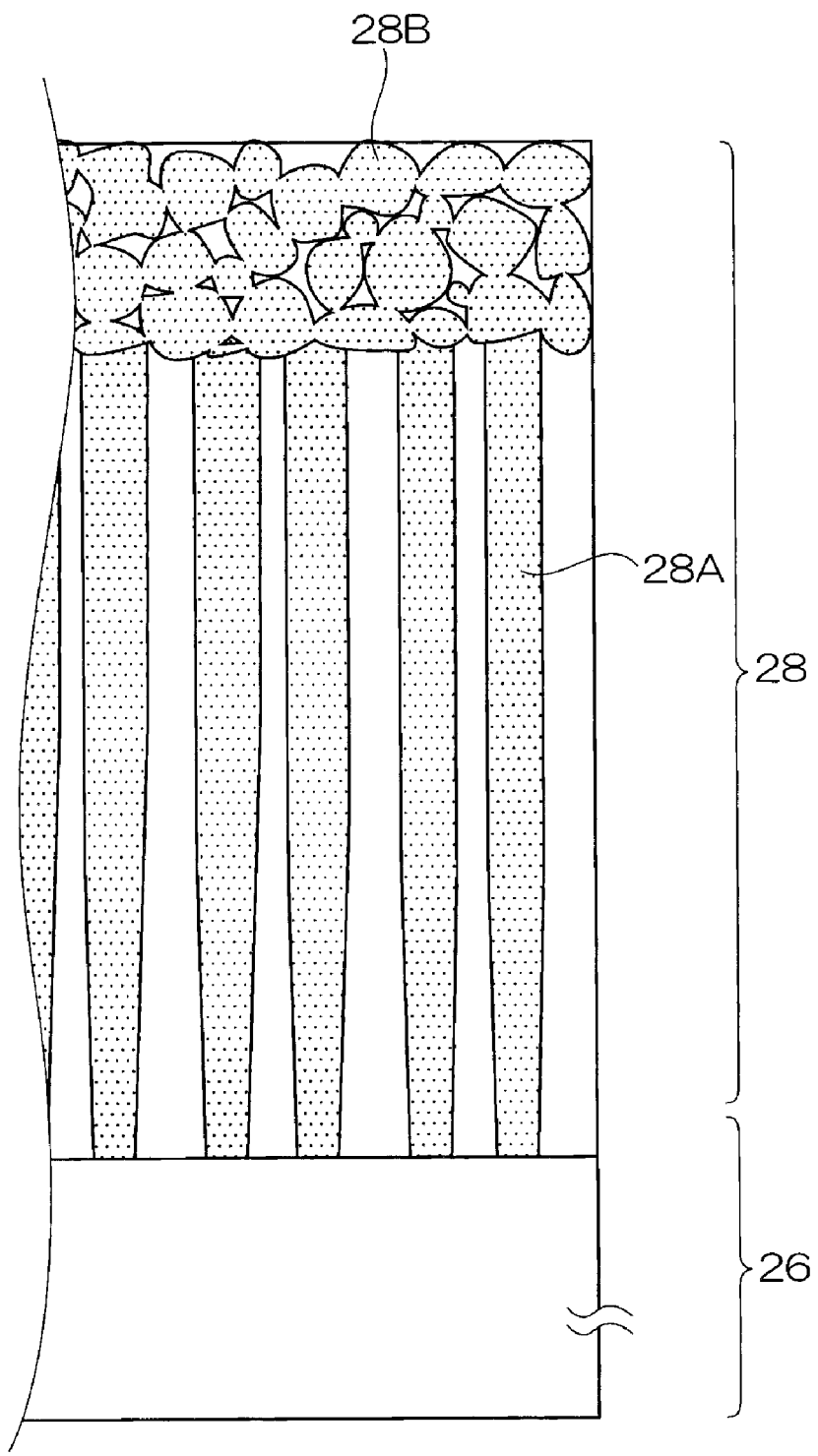
FIG. 11 is a schematic diagram graphically illustrating an example of the crystalline structure of a scintillator layer.

Further, when a material including cesium iodide (CsI) or the like is used as scintillator layer 28, and the radiation panel is disposed such that radiation that has transmitted through TFT substrate 26 is incident at scintillator layer 28, it is preferable that a columnar crystal region formed from columnar crystal 28A is provided at the radiation incident side of scintillator layer 28 (the TFT substrate 26 side) and that a non-columnar crystal region formed from non-columnar crystal 28B is provided at the opposite side to the radiation incident side of scintillator layer 28, as shown in FIG. 11. In addition, scintillator layer 28 configured as shown in FIG. 11 is an example of a light emitting portion as recited in claim 12. Further, when a material including CsI is used as scintillator layer 28, scintillator layer 28 thus configured is an example of a light emitting portion as recited in claim 13.

By, as described above, forming scintillator layer 28 from a columnar crystal region formed from columnar crystal 28A and a non-columnar crystal region and disposing the columnar crystal region from which highly efficient light emission can be obtained at the TFT substrate 26 side, light generated at scintillator layer 28 is channeled along the gaps in columnar crystal 28A and emitted toward the TFT substrate 26 side. Since diffusion of the light emitted toward the TFT substrate 26 side is suppressed, blurring of radiographic images detected by the radiation detection panel is suppressed. Further, light that arrives at the deeper portion (the non-columnar crystal region) of scintillator layer 28 is reflected by non-columnar crystal 28B toward the side of TFT substrate 26, as a result, the amount of light incident on TFT substrate 26 is increased and the detection efficiency with respect to light emitted from scintillator layer 28 is improved.

In addition, if t1 is the thickness of the columnar crystal region positioned at the radiation incident side of scintillator layer 28 and t2 is the thickness of the non-columnar crystal region positioned at the opposite side to radiation incident side of scintillator layer 28, t1 and t2 preferably satisfy the following relationship.

$$0.01 \leq (t2/t1) \leq 0.25$$

When the thickness t1 of the columnar crystal region and the thickness t2 of the non-columnar crystal region satisfy the above relationship, the relative proportions of the columnar crystal region that has highly efficient light emission and that prevents diffusion of light and the non-columnar crystal region that reflects light in the thickness direction of scintillator layer 28 fall within a favorable range and the light emission efficiency of scintillator layer 28, the detection efficiency with respect to light emitted at scintillator layer 28, and the resolution of radiographic images are improved. Since a region with poor light emission efficiency is increased when the thickness t2 of the non-columnar crystal region becomes too large, which can lead to reduction in the sensitivity of radiation detection panel 20, it is more preferable that (t2/t1) is in the range of from 0.02 to 0.1.

In addition, while scintillator layer 28 having a columnar crystal region and a non-columnar crystal region formed contiguously has been explained above as an example of a light emitting portion as recited in claims 12 and 13, a configuration may be adopted in which a light-reflective layer formed from aluminum or the like is provided instead of the non-columnar crystal region and only the columnar crystal region is formed in scintillator layer 28, or other configurations may be adopted.

Further, while radiation detection panel 20 employing an indirect conversion method, whereby radiation is first converted to light at scintillator layer 28 and then the converted light is converted to charge and accumulated at photoconductive layers 30, has been explained above as an example of the radiation detection panel according to the present invention, the present invention is not limited to this. For example, a radiation detection panel may be used that employs a direct conversion method, whereby radiation is converted directly to charge and accumulated by a sensor portion using amorphous selenium or the like.

Figure 12:
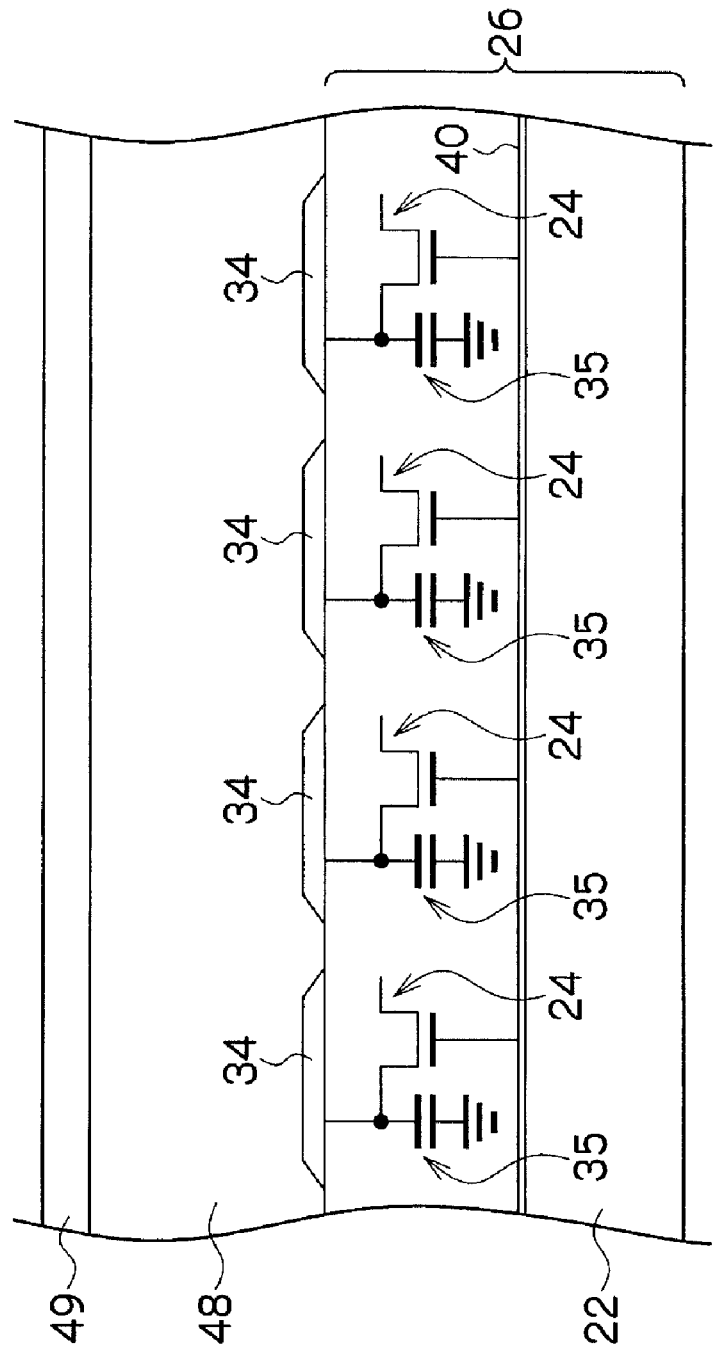
FIG. 12 is a sectional view showing a variant example of a schematic configuration of a radiation detection panel.

An example of a direct conversion radiation detection panel is shown in FIG. 12. In this radiation detection panel, photoconductive layer 48, which converts incident radiation into electrical charge, is formed on TFT substrate 26. A compound having as a main component at least one of amorphous selenium, $Bi_{12}MO_{20}$(M:Ti, Si, Ge), $Bi_4M_3O_{12}$(M:Ti, Si, Ge), $Bi_2O_3$, $BiMO_4$(M:Nb, Ta, V), $Bi_2WO_6$, $Bi_{24}B_2O_{39}$, ZnO, ZnS, ZnSe, ZnTe, $MNbO_3$(M:Li, Na, K), PbO, $HgI_2$, $PbI_2$, CdS, CdSe, CdTe, $BiI_3$, or GaAs is used for photoconductive layer 48, and a non-crystalline (amorphous) material having high dark resistance, exhibiting favorable photoconductivity with respect to x-rays and capable of being formed as a film over a large surface area by vacuum deposition, is preferable. Bias electrode 49, which is for applying bias voltage to photoconductive layer 48, is formed on photoconductive layer 48 on the surface side thereof. Further, similarly to in an indirect conversion radiation detection panel, charge collection electrodes 34 that collect charge generated at photoconductive layer 48 are formed on TFT substrate 26. However, in TFT substrate 26 in a direct conversion radiation detection panel, charge storage capacitors 35 are provided, which store the charge collected at the respective charge collection electrodes 34. Charge stored at charge storage capacitors 35 is read out by switching elements 24 being switched on.

The configurations of electronic cassettes 10, 90 and radiation detection panel 20 explained in the above embodiments are given as examples and it should be evident that they may be altered as appropriate to the extent that they do not depart from the gist of the present invention.

In the present invention as described above, since a first end portion of a connection portion is attached to a side portion of a panel unit accommodating a radiation detection panel so as to be rotatable around a first axis that is substantially parallel to an irradiation surface of the panel unit, and a second end portion of the connection portion is attached to a control unit accommodating a control section and a power source section so as to be rotatable around a second axis that is substantially parallel to the first axis, it is possible to suppress increases in the temperature of the radiation detection panel without causing any complication of configuration or increase in electrical power consumption, and the invention has an exceptional effect whereby image capture is possible in a wide variety of situations.

What is claimed is:

1. A radiographic imaging device, comprising:
a panel unit accommodating a radiation detection panel;
a control unit accommodating a control section and a power source section; and
a connection portion, wherein a first end portion of the connection portion is attached to a side portion of the panel unit so as to be rotatable around a first axis that is substantially parallel to an irradiation surface of the panel unit, and a second end portion of the connection portion is attached to the control unit so as to be rotatable around a second axis that is substantially parallel to the first axis;
wherein at least one of the first end portion or the second end portion of the connection portion is movably attached to the panel unit or the control unit, such that the first end portion or the second end portion of the connection portion slides along a side portion of the panel unit or the control unit.

2. The radiographic imaging device of claim 1, wherein:
the radiation detection panel detects radiation that has transmitted through an object to be imaged and irradiated the irradiation surface of the panel unit; and
the control section comprises a drive section that drives the radiation detection panel such that a radiographic signal is output by the radiation detection panel and a signal processing section that converts the radiographic signal output by the radiation detection panel to radiographic image data expressing the distribution of an irradiated radiation dose and outputs the radiographic image data.

3. The radiographic imaging device of claim 1, wherein the connection portion is rotatable between a first state in which the irradiation surface of the panel unit contacts the control unit and a second state in which a side portion of the panel unit and a side portion of the control unit face each other with a gap therebetween.

4. The radiographic imaging device of claim 1, wherein a range of movement of the at least one of the first end portion or the second end portion of the connection portion relative to the panel unit or the control unit is set such that, in the second state, the panel unit or the control unit is rotatable around the first axis or the second axis without being impeded by the other of the panel unit or the control unit.

5. The radiographic imaging device of claim 1, wherein the control section accommodated in the control unit further comprises a communication section that communicates with the exterior.

6. The radiographic imaging device of claim 1, wherein:
the control unit is provided with a display portion that is configured to display information; and
the control section accommodated in the control unit further comprises a display control section that is configured to effect display of information at the display portion.

7. The radiographic imaging device of claim 3, wherein:
a display portion that is configured to display information is provided such that a display screen is exposed at an external peripheral portion of the control unit;
the control section accommodated in the control unit further comprises a display control section that is configured to effect display of information at the display portion; and
in the first state, the display portion of the control unit contacts the irradiation surface of the panel unit.

8. The radiographic imaging device of claim 6, wherein:
the control section accommodated in the control unit further comprises a storage section that is adapted to store information including radiographic image data; and
the display control section effects display of the information including radiographic image data stored at the storage section, at the display portion.

9. The radiographic imaging device of claim 8, wherein:
the control unit is provided with an input portion for inputting information; and
the display control section selects information to be displayed at the display portion based on information input via the input portion.

10. The radiographic imaging device of claim 1, wherein the radiation detection panel comprises a radiation conversion layer and a switching layer, wherein a substrate that forms the switching layer is formed from a material through which radiation transmits.

11. The radiographic imaging device of claim 1, wherein the radiation detection panel comprises a light emitting portion that absorbs radiation and emits light and a detection portion that detects light emitted from the light emitting portion, and the light emitting portion has a columnar crystal structure portion.

12. The radiographic imaging device of claim 11, wherein the light emitting portion that has a columnar crystal structure portion includes CsI.

13. The radiographic imaging device of claim 1, wherein the panel unit and the control unit are rotatably connected with the two connection portions attached therebetween.

\* \* \* \* \*